(12) United States Patent
Lee

(10) Patent No.: US 9,825,233 B2
(45) Date of Patent: *Nov. 21, 2017

(54) HETEROCYCLIC COMPOUND AND ORGANIC LIGHT-EMITTING DEVICE INCLUDING THE SAME

(71) Applicant: SAMSUNG DISPLAY CO., LTD., Yongin, Gyeonggi-do (KR)

(72) Inventor: Jung-Sub Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 385 days.

This patent is subject to a terminal disclaimer.

(21) Appl. No.: 14/012,545

(22) Filed: Aug. 28, 2013

(65) Prior Publication Data
US 2014/0151650 A1   Jun. 5, 2014

(30) Foreign Application Priority Data

Dec. 4, 2012  (KR) .................. 10-2012-0139820

(51) Int. Cl.
| | | |
|---|---|---|
| H01L 51/00 | (2006.01) | |
| C07D 471/04 | (2006.01) | |
| C07D 519/00 | (2006.01) | |
| C07F 7/08 | (2006.01) | |
| H01L 51/50 | (2006.01) | |

(52) U.S. Cl.
CPC ........ H01L 51/0067 (2013.01); C07D 471/04 (2013.01); C07D 519/00 (2013.01); C07F 7/0812 (2013.01); H01L 51/0071 (2013.01); H01L 51/0072 (2013.01); H01L 51/0074 (2013.01); H01L 51/0094 (2013.01); H01L 51/0081 (2013.01); H01L 51/0085 (2013.01); H01L 51/5016 (2013.01)

(58) Field of Classification Search
None
See application file for complete search history.

(56) References Cited

U.S. PATENT DOCUMENTS

| | | | | |
|---|---|---|---|---|
| 9,082,988 B2* | 7/2015 | Lee | .................. | H01L 51/5016 |
| 2002/0158242 A1 | 10/2002 | Son et al. | | |
| 2006/0113905 A1* | 6/2006 | Nakamura | .......... | H01L 27/3244 |
| | | | | 313/511 |
| 2006/0131562 A1* | 6/2006 | Li | .................. | H01L 51/002 |
| | | | | 257/40 |
| 2011/0108819 A1* | 5/2011 | Kathirgamanathan | .................. | |
| | | | | C07D 263/57 |
| | | | | 257/40 |
| 2011/0278555 A1 | 11/2011 | Inoue et al. | | |
| 2011/0279020 A1 | 11/2011 | Inoue et al. | | |
| 2014/0231759 A1* | 8/2014 | Kim | .................. | H01L 51/5262 |
| | | | | 257/40 |

FOREIGN PATENT DOCUMENTS

| | | | | | |
|---|---|---|---|---|---|
| JP | 2007189001 A | * | 7/2007 | ............ | H01L 51/50 |
| KR | 10-2004-0051507 A | | 6/2004 | | |
| KR | 10-2011-092262 A | | 8/2011 | | |
| KR | 10-2012-0034648 A | | 4/2012 | | |
| KR | 10-2012-0044517 A | | 5/2012 | | |
| KR | 10-2012-0044529 A | | 5/2012 | | |

* cited by examiner

*Primary Examiner* — J. L. Yang
(74) *Attorney, Agent, or Firm* — H.C. Park & Associates, PLC

(57) ABSTRACT

A heterocyclic compound represented by Formula 1 below and an organic light-emitting device including the heterocyclic compound are described.

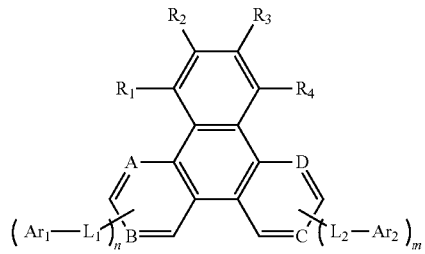

<Formula 1>

In Formula 1, R1 to R4 may be each independently one of a hydrogen atom, a deuterium atom, C5-C60 alkyl, C5-C60 aryl and C6-C60 condensed polycyclic; L1 and L2 may be each independently one of a single bond, C5-C60 aryl, C3-C60 heteroaryl and C6-C60 condensed polycyclic; Ar1 and Ar2 may be each independently one of C5-C60 aryl, C3-C60 heteroaryl and C6-C60 condensed polycyclic; A, B, C and D may be each independently one of —CH= and —N=, excluding that all A, B, C and D are —CH=; and m and n may be each independently an integer of 0 to 3, excluding that all m and n are zero, wherein any of the above alkyl groups, aryl groups, condensed polycyclic groups and heteroaryl groups may be substituted or unsubstituted.

15 Claims, 1 Drawing Sheet

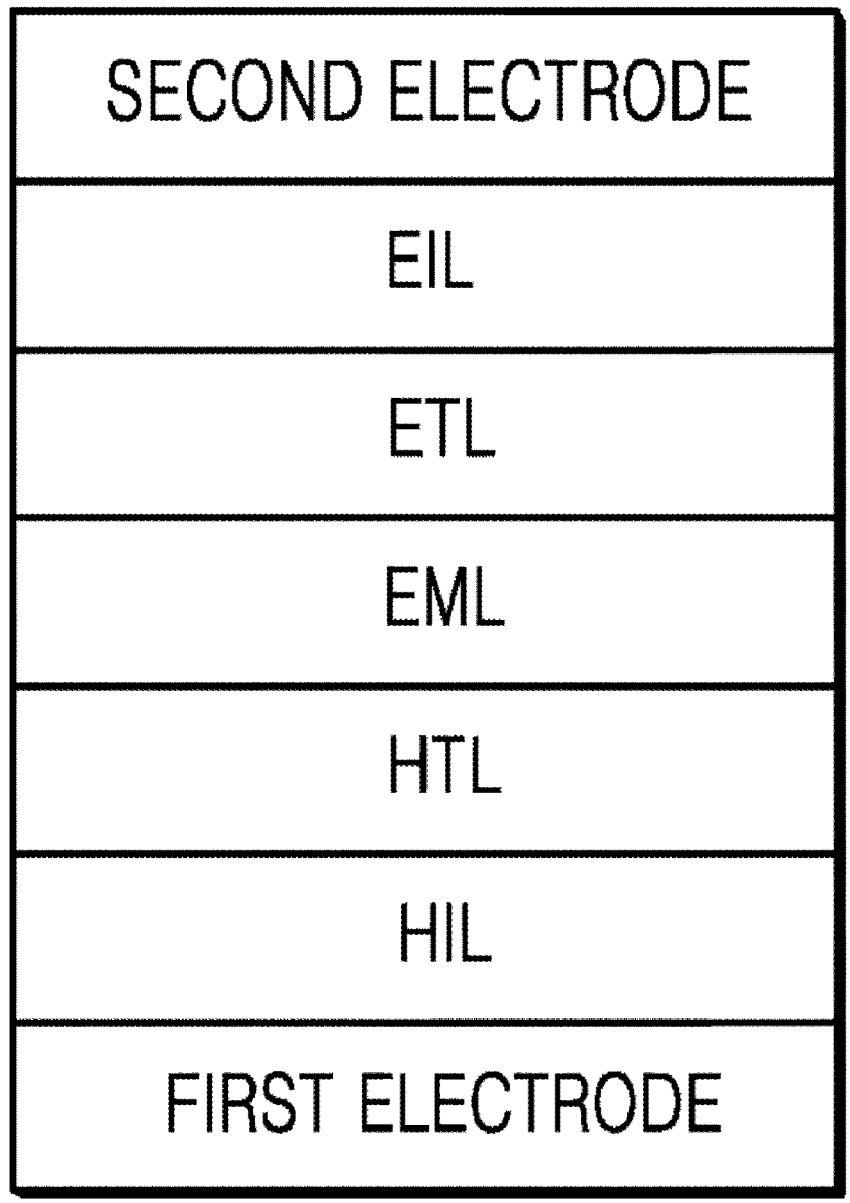

HETEROCYCLIC COMPOUND AND ORGANIC LIGHT-EMITTING DEVICE INCLUDING THE SAME

CLAIM OF PRIORITY

This application makes reference to, incorporates the same herein, and claims all benefits accruing under 35 U.S.C. §119 from an application for HETEROCYCLIC COMPOUND AND ORGANIC LIGHT-EMITTING DEVICE INCLUDING THE SAME earlier filed in the Korean Intellectual Property Office on 4 Dec. 2012 and there duly assigned Serial No. 10-2012-0139820.

BACKGROUND OF THE INVENTION

Field of the Invention

The present invention relates to a heterocyclic compound and an organic light-emitting device including the heterocyclic compound.

Description of the Related Art

Organic light-emitting devices (OLEDs), which are self-emitting devices, have advantages such as wide viewing angles, excellent contrast, quick response, high brightness and excellent driving voltage characteristics, and they can provide multicolored images.

A typical OLED has a structure including a substrate and an anode, a hole transport layer (HTL), an emission layer (EML), an electron transport layer (ETL), and a cathode, which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

A major factor that affects luminescent efficiency of an OLED is the type of luminescent material used. Although fluorescent materials have been widely used as luminescent materials so far, development of a phosphorescent material able to improve luminescent efficiency up to four times based on theoretical electroluminescence mechanisms is an effective method for luminescent efficiency improvement. Iridium (III) complex-based phosphorescent materials have been widely known so far, and bis(2-(2'-benzothienyl)-pyridinato-N,C3')iridium(acetylacetonate)) ((acac)Ir(btp)$_2$), tris(2-phenylpyridine)iridium (Ir(ppy)$_3$), and bis[2-(4,6-difluorophenyl)pyridinato-C2,N](picolinato)iridium (Firpic) are available for red, green and blue emission, respectively.

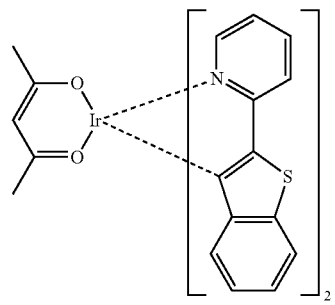

(acac)Ir(btp)$_2$

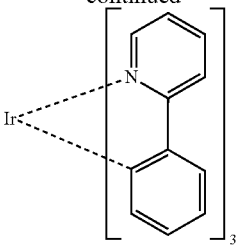

Ir(PPY)$_3$

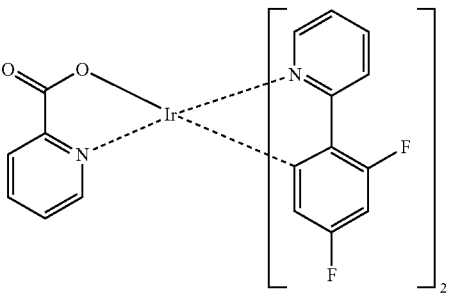

Firpic 4, 4'-N,N'-dicarbazole-biphenyl (CBP) is the most widely known phosphorescent host material so far. A high-efficiency organic light-emitting device with a hole blocking layer formed from 2,9-dimethyl-4,7-diphenyl-1,10-phenanthroline (BCP) or bis(2-methyl-8-quinolinato-N1,O8)-(1,1'-biphenyl-4-olato)aluminum (BAlq), and a high-performance OLED (Pioneer, Japan) using a BAlq derivative as a host are disclosed.

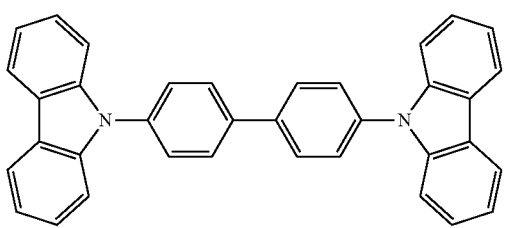

CBP

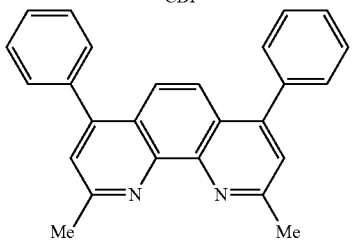

BCP

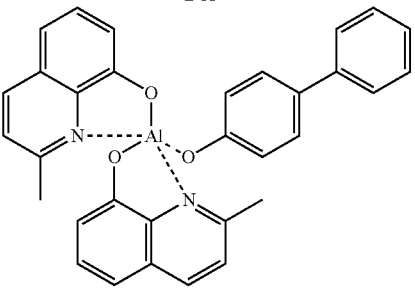

BAlq

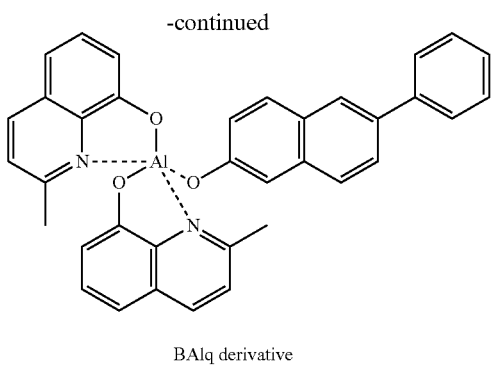

BAlq derivative

Although they have advantageous light-emitting characteristics, these existing luminescent materials have low glass transition temperatures and poor thermal stability, and thus they may be deteriorated during a high-temperature deposition process under vacuum. The power efficiency of an OLED may be represented as: Power efficiency=(π/Voltage)×Current Efficiency. That is, power efficiency is inversely proportional to voltage, and the power efficiency of the OLED should be high in order to achieve reduced power consumption. In practice, an OLED using a common phosphorescent (host) material such as BAlq or CBP may have a considerably higher current efficiency (cd/A) but also have a higher driving voltage, as compared with an OLED using a fluorescent material, and thus this arrangement is not advantageous in terms of power efficiency (lm/w). OLEDs using such a host material from the existing art are also not satisfactory in terms of lifetime. Therefore, there is a demand for development of a more stable host material with improved characteristics, allowing for both good current efficiency and good power efficiency.

SUMMARY OF THE INVENTION

The present invention provides a novel organic light-emitting compound having a rigid backbone and being capable of imparting to OLEDs improved luminescent efficiency and long lifetimes as compared with OLED properties imparted by host materials described in the existing art. The organic light-emitting compound of the present invention also imparts to OLEDs appropriate color coordinates and high power efficiency.

According to an embodiment of the present invention, there is provided a heterocyclic compound represented by Formula 1 below:

<Formula 1>

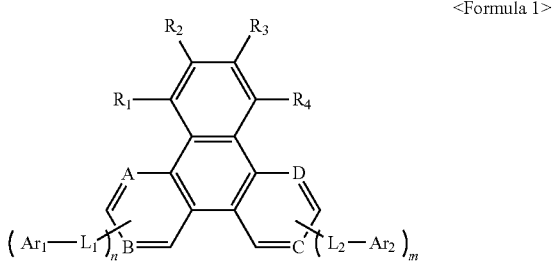

$R_1$ to $R_4$ in Formula 1 being each independently one of a hydrogen atom, a deuterium atom, a substituted or unsubstituted C5-C60 alkyl group, a substituted or unsubstituted C5-C60 aryl group and a substituted or unsubstituted C6-C60 condensed polycyclic group;

$L_1$ and $L_2$ in Formula 1 being each independently one of a single bond, a substituted or unsubstituted C5-C60 aryl group, a substituted or unsubstituted C3-C60 heteroaryl group and a substituted or unsubstituted C6-C60 condensed polycyclic group;

$Ar_1$ and $Ar_2$ in Formula 1 being each independently one of a substituted or unsubstituted C5-C60 aryl group, a substituted or unsubstituted C3-C60 heteroaryl group and a substituted or unsubstituted C6-C60 condensed polycyclic group;

A, B, C, and D in Formula 1 being each independently one of —CH= and —N=, excluding that all A, B, C, and D are —CH=; and m and n are each independently an integer of 0 to 3, excluding that all m and n are zero.

According to another embodiment of the present invention, there is provided an organic light-emitting device including: a first electrode; a second electrode; and an organic layer between the first electrode and the second electrode, the organic layer including the above-described heterocyclic compound of Formula 1.

According to embodiment aspect of the present invention, there is provided a flat panel display device including the above-described organic light-emitting device, the first electrode of the organic light-emitting device being electrically connected to one of a source electrode and a drain electrode of a thin-film transistor.

BRIEF DESCRIPTION OF THE DRAWING

A more complete appreciation of the invention and many of the attendant advantages thereof will be readily apparent as the same becomes better understood by reference to the following detailed description when considered in conjunction with the accompanying drawings, in which like reference symbols indicate the same or similar components, wherein:

The FIGURE is a schematic view of a structure of an organic light-emitting device according to an embodiment of the present invention.

DETAILED DESCRIPTION OF THE INVENTION

As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a novel heterocyclic compound represented by Formula 1 below:

<Formula 1>

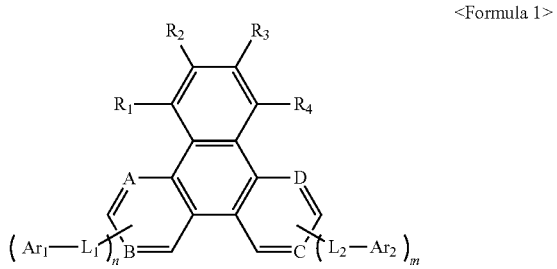

In Formula 1 above, $R_1$ to $R_4$ are each independently one of a hydrogen atom, a deuterium atom, a substituted or unsubstituted C5-C60 alkyl group, a substituted or unsubstituted C5-C60 aryl group, and a substituted or unsubstituted C6-C60 condensed polycyclic group;

$L_1$ and $L_2$ are each independently one of a single bond, a substituted or unsubstituted C5-C60 aryl group, a substituted or unsubstituted C3-C60 heteroaryl group, and a substituted or unsubstituted C6-C60 condensed polycyclic group;

$Ar_1$ and $Ar_2$ are each independently one of a substituted or unsubstituted C5-C60 aryl group, a substituted or unsubstituted C3-C60 heteroaryl group, and a substituted or unsubstituted C6-C60 condensed polycyclic group;

A, B, C, and D are each independently one of —CH= and —N=, excluding that all A, B, C, and D are —CH=; and m and n are each independently an integer of 0 to 3, excluding that all m and n are zero.

In some embodiments, the heterocyclic compound of Formula 1 above may be used as a green or red phosphorescent material in an organic light-emitting device. The heterocyclic compound of Formula 1 has a high glass transition temperature (Tg) or melting point due to the introduction of the heterocyclic group. Thus, the heterocyclic compound has high resistance to phase change or deformation when Joule's heat is generated in an organic layer, between organic layers, or between an organic layer and a metal electrode as light emission occurs, and the associated OLED has high durability in high-temperature environments. Accordingly, an organic light-emitting device manufactured using the heterocyclic compound of Formula 1 may have high durability when stored or operated.

The substituents of the heterocyclic compound of Formula 1 now will be described in greater detail.

In some embodiments, $R_1$ to $R_4$ in Formula 1 may be each independently one of a hydrogen atom and a deuterium atom.

In some other embodiments, $L_1$ and $L_2$ in Formula 1 may be each independently one of a single bond and a group represented by one of Formulae 2a to 2c below:

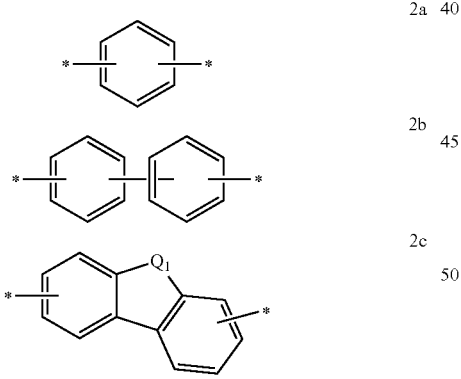

2a

2b

2c

In Formulae 2a to 2c, $Q_1$ is —$CR_{30}R_{31}$;

$R_{30}$ and $R_{31}$ are each independently one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, halogen group, a cyano group, a nitro group, a hydroxy group, and a carboxy group; and

* indicates a binding site.

In some other embodiments, $Ar_1$ and $Ar_2$ in Formula 1 may be each independently a group represented by one of Formulae 3a to 3j below:

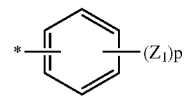

3a

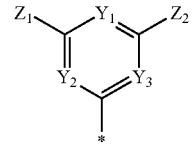

3b

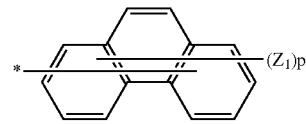

3c

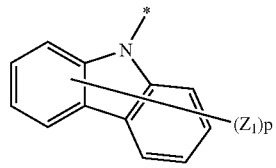

3d

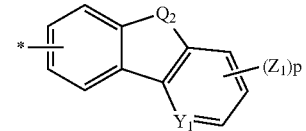

3e

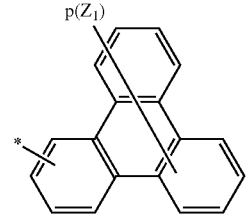

3f

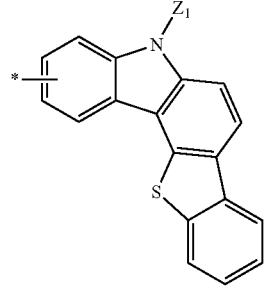

3g

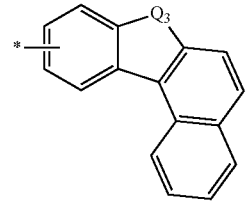

3h

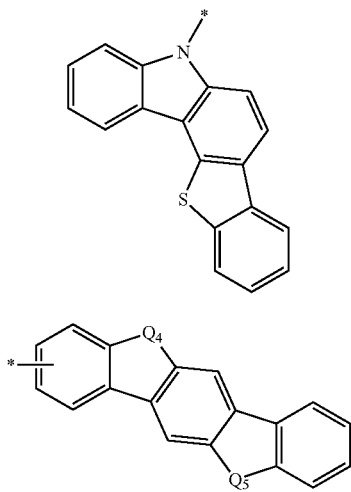

3i

3j

In Formulae 3a to 3j, $Q_2$ to $Q_5$ are each independently one of —$CR_{30}R_{31}$—, —$NR_{32}$—, —S—, and —O—;

$Z_1$, $Z_2$, $R_{30}$, $R_{31}$, and $R_{32}$ are each independently one of a hydrogen atom, a deuterium atom, a substituted or unsubstituted C1-C20 alkyl group, a substituted or unsubstituted C5-C20 aryl group, a substituted or unsubstituted C3-C20 heteroaryl group, a substituted or unsubstituted C6-C20 condensed polycyclic group, an amino group substituted with one of a C3-C20 heteroaryl group and a C5-C20 aryl group, a halogen group, a cyano group, a nitro group, a hydroxy group, —$Si(R_{40})_3$ and a carboxy group;

$R_{40}$ is one of a substituted or unsubstituted C1-C20 alkyl group, a substituted or unsubstituted C5-C20 aryl group, a substituted or unsubstituted C3-C20 heteroaryl group and a substituted or unsubstituted C6-C20 condensed polycyclic group;

$Y_1$, $Y_2$, and $Y_3$ are each independently one of —CH= and —N=;

p is an integer of 1 to 9; and

* indicates a binding site.

In some other embodiments, A and D in Formula 1 may be all —N=; and B and C may be all —CH=.

Hereinafter, substituents described with reference to the formulae will now be described in detail. In this regard, the numbers of carbons in substituents are presented only for illustrative purposes and do not limit the characteristics of the substituents.

The unsubstituted C1-C60 alkyl group used herein may be linear or branched. Examples of the alkyl group are, but are not limited to, a methyl group, an ethyl group, a propyl group, an isobutyl group, a sec-butyl group, a pentyl group, an iso-amyl group, a hexyl group, a heptyl group, an octyl group, a nonyl group, and a dodecyl group. At least one hydrogen atom of the alkyl group may be substituted with a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, or a C4-C16 heteroaryl group.

The unsubstituted C2-C60 alkenyl group indicates an unsaturated alkyl group having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propyne, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group, at least one hydrogen atom in the cycloalkyl group being substituted with a substituent described above in conjunction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as one of those described above in conjunction with the alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the substituted or unsubstituted C6-C60 aryl group are a phenyl group, a C1-C10 alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a C1-C10 alkyl biphenyl group, a C1-C10 alkoxybiphenyl group, a o-, m-, and p-tolyl group, an o-, m-, and p-cumenyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a C1-C10 alkylnaphthyl group (for example, methylnaphthyl group), a C1-C10 alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C3-C60 heteroaryl group used herein includes one, two or three hetero atoms selected from N, O, P and S. At least two rings may be fused to each other or linked to each other by a single bond. Non-limiting examples of the unsubstituted C4-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C6-C60 aryloxy group is a group represented by —$OA_1$ wherein $A_1$ may be a C6-C60 aryl group. An example of the aryloxy group is a phenoxy group. At least one hydrogen atom in the aryloxy group may be substituted with a substituent described above in conjunction with the C1-C60 alkyl group.

The unsubstituted C6-C60 arylthio group is a group represented by —$SA_1$ wherein $A_1$ may be a C6-C60 aryl group. Non-limiting examples of the arylthio group are a benzenethio group and a naphthylthio group. At least one hydrogen atom in the arylthio group may be substituted with a substituent described above in conjunction with the C1-C60 alkyl group.

The unsubstituted C6-C60 condensed polycyclic group used herein refers to a substituent including at least two rings, at least one aromatic ring and/or at least one non-aromatic ring being fused to each other, or refers to a substituent having an unsaturated group in a ring that may not form a conjugate structure. The unsubstituted C6-C60 condensed polycyclic group is distinct from an aryl group or a heteroaryl group because it is non-aromatic.

In some embodiments, the heterocyclic compound of Formula 1 above may be one of Compounds 1 to 30 below, but it is not limited thereto:

1

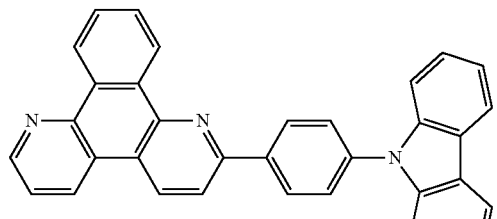

2

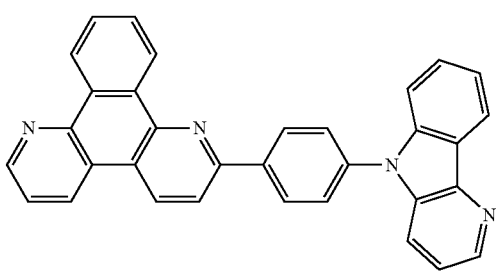

3

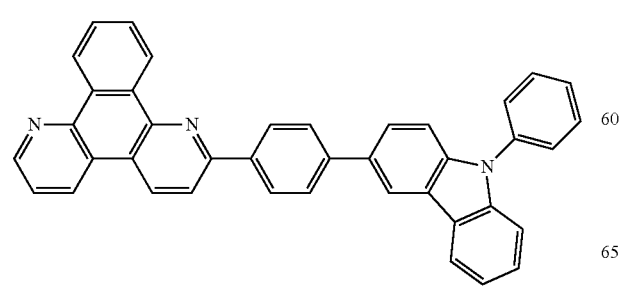

4

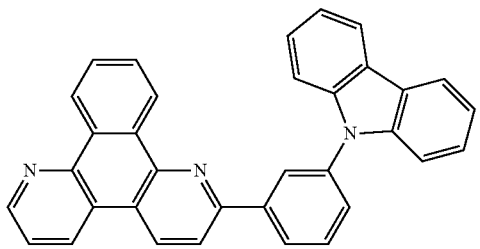

5

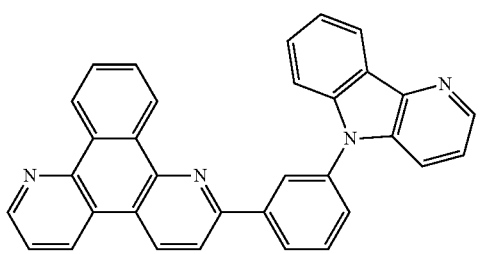

6

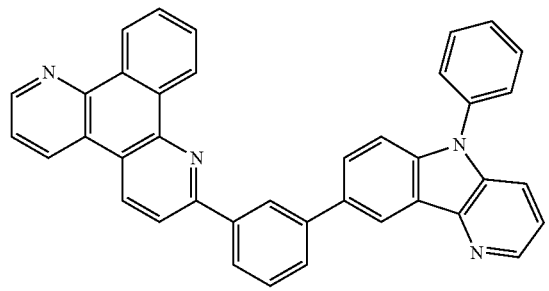

7

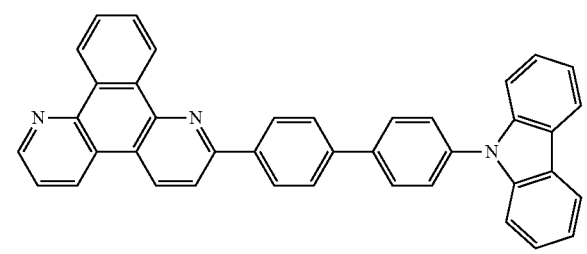

8

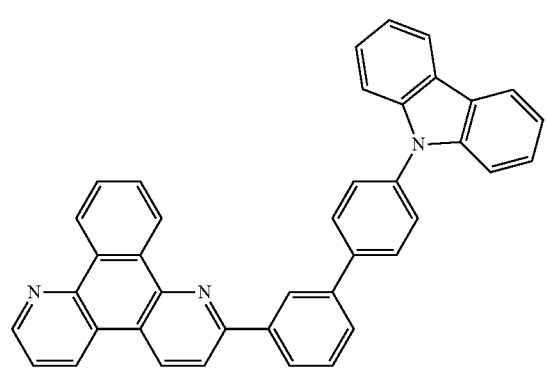

9
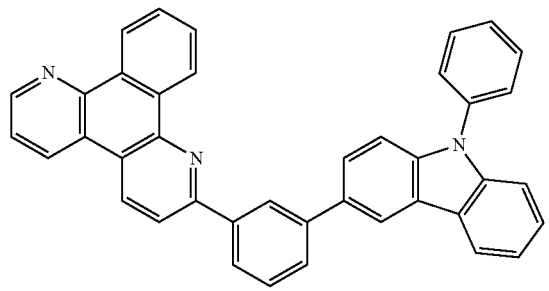
10
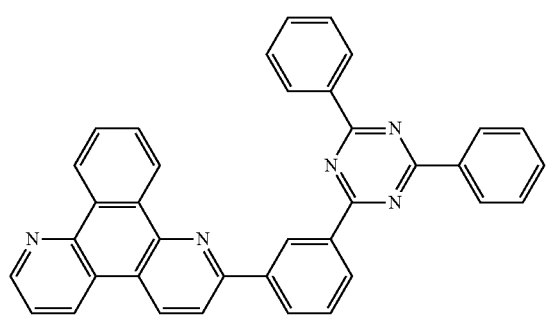
11
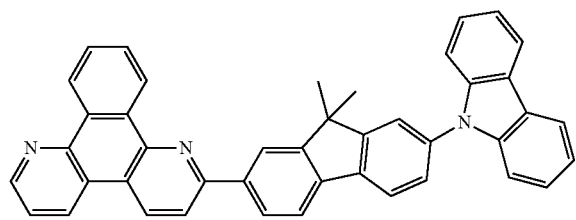
12
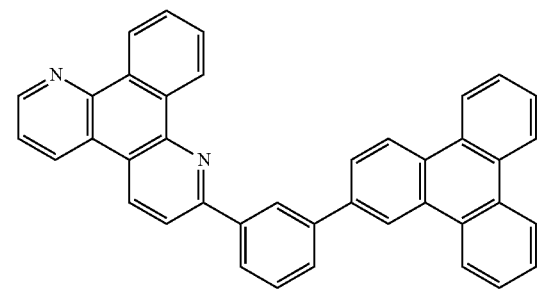
13
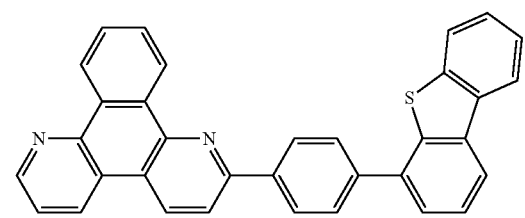
14
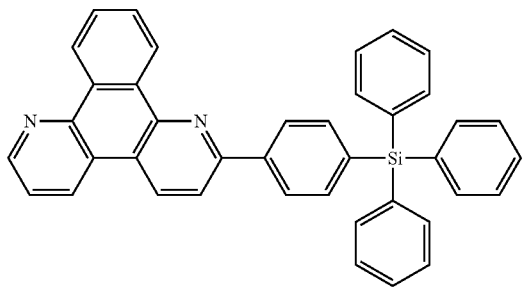
15
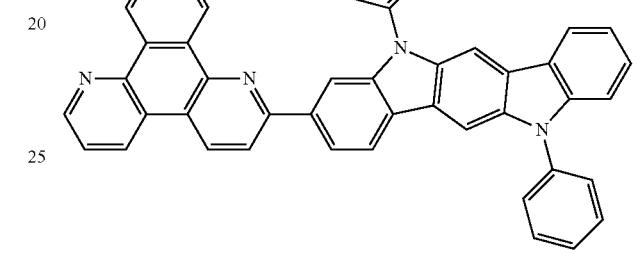
16
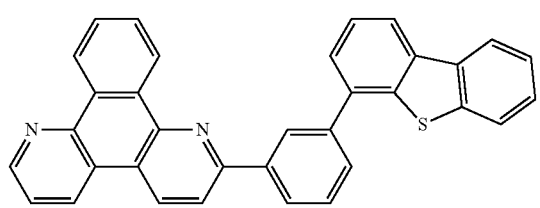
17
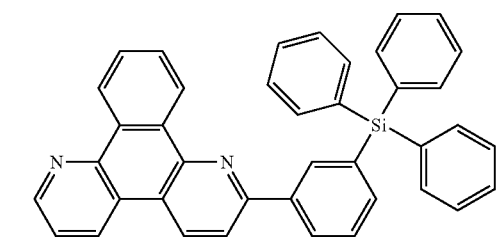
18
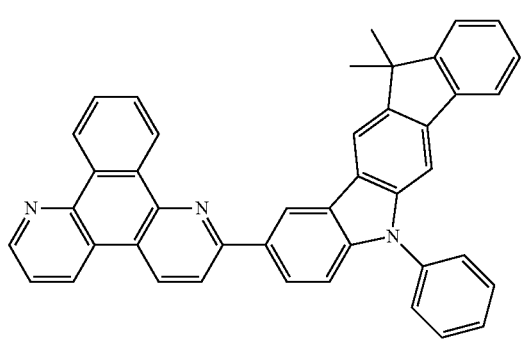

19
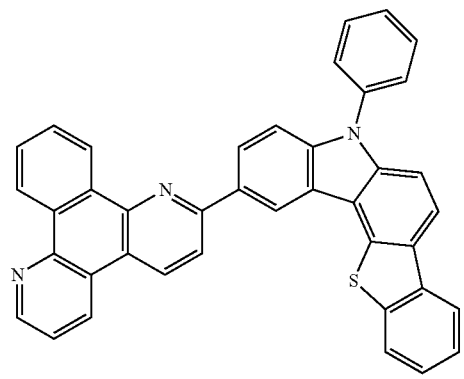
20
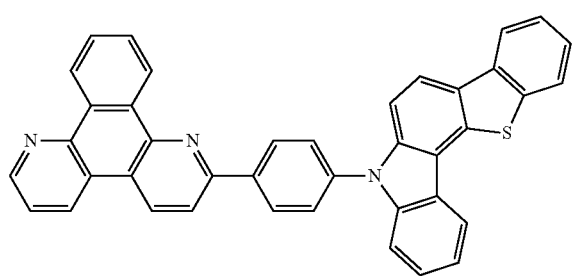
21
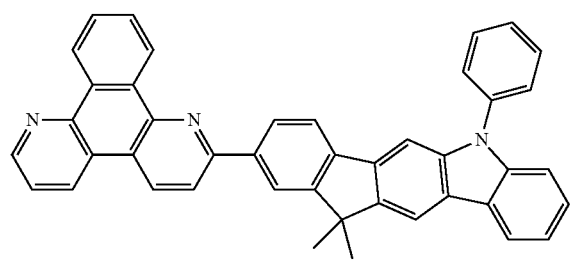
22
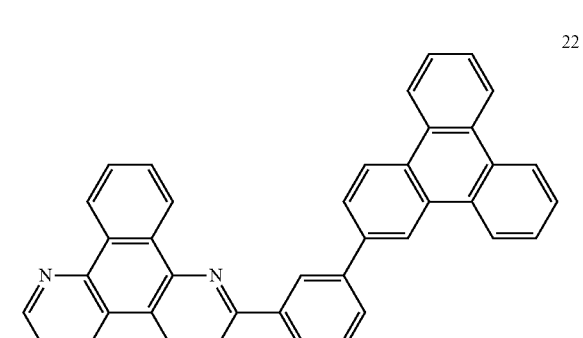
23
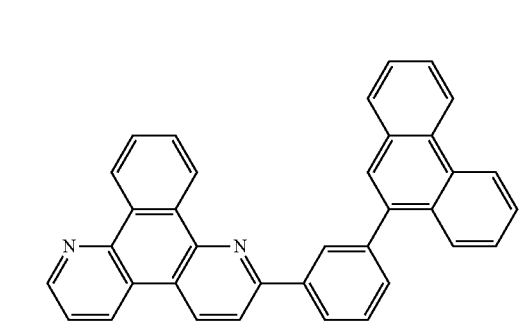
24
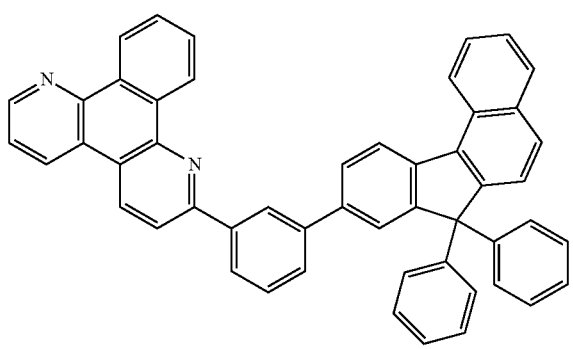
25
26
27
28

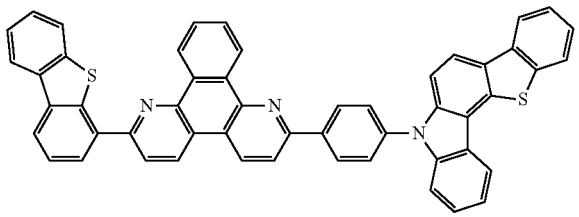

29

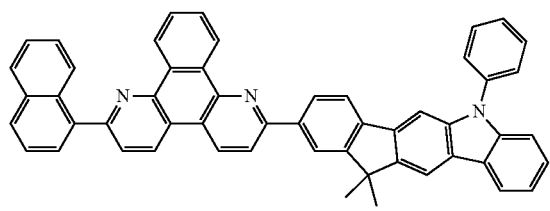

30

According to another embodiment of the present invention, there is provided an organic light-emitting device including a first electrode, a second electrode, and an organic layer disposed between the first electrode and the second electrode, the organic layer including the compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

In some embodiments, the organic layer may be used as an emission layer. For example, the organic layer may be a phosphorescent green layer or a phosphorescent red layer.

In some embodiments, the organic light-emitting device may include an electron injection layer, an electron transport layer, an emission layer, a hole injection layer, a hole transport layer, or a functional layer having both hole injection and transport capabilities; and the emission layer may include the compound of Formula 1 above and may further include an anthracene-based compound, an arylamine-based compound or a styryl-based compound.

In some other embodiments, the organic light-emitting device may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include a charge-generating material. In some embodiments, the charge-generating material may be a p-dopant, and the p-dopant may be a quinine derivative, a metal oxide, or a cyano group-containing compound.

In some embodiments, the organic layer may include an electron transport layer, and the electron transport layer may include an electron-transporting organic compound and a metal complex. The metal complex may be a lithium (Li) complex.

The term "organic layer" as used herein refers to a single layer and/or a plurality of layers disposed between the first and second electrodes of the organic light-emitting device.

The organic layer may include an emission layer, and the emission layer may include the compound of Formula 1 described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound of Formula 1.

The FIGURE is a schematic sectional view of an organic light-emitting device according to an embodiment of the present invention. Hereinafter, a structure of an organic light-emitting device according to an embodiment of the present invention and a method of manufacturing the same will now be described with reference to the FIGURE.

A substrate (not shown) may be any substrate that is used in existing organic light emitting devices. In some embodiments, the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as indium tin oxide (ITO), indium zinc oxide (IZO), $SnO_2$, and ZnO may be used to form the first electrode. The first electrode may be formed as a reflective electrode using one of magnesium (Mg), aluminum (Al), aluminum-lithium (Al—Li), calcium (Ca), magnesium-indium (Mg—In), magnesium-silver (Mg—Ag), and the like.

The first electrode may have a single-layer structure or a multi-layer structure including at least two layers. For example, the first electrode may have a three-layered structure of ITO/Ag/ITO, but it is not limited thereto.

One or more organic layer(s) are disposed on the first electrode.

The organic layer may include at least one of a hole injection layer (HIL), a hole transport layer (HTL), a buffer layer (not shown), an emission layer (EML), an electron transport layer (ETL) and an electron injection layer (EIL).

The HIL may be formed on the first electrode by one of vacuum deposition, spin coating, casting, Langmuir-Blodgett (LB) deposition, and the like.

When the HIL is formed using vacuum deposition, vacuum deposition conditions may vary according to the compound that is used to form the HIL and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris (3-methylphenylphenylamino) triphenylamine (m-MTDATA), N,N'-di(1-naphthyl)-N,N'-diphenylbenzidine (NPB), 4,4',4"-tris(diphenylamino)triphenylamine (TDATA), 4,4',4"-tris[2-naphthyl(phenyl)amino]triphenylamine (2T-NATA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

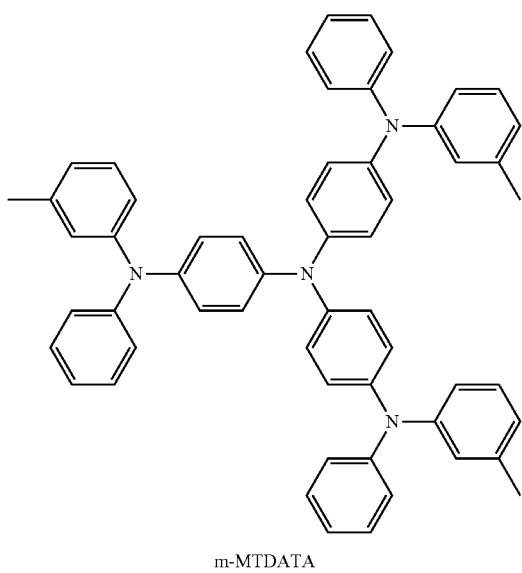

m-MTDATA

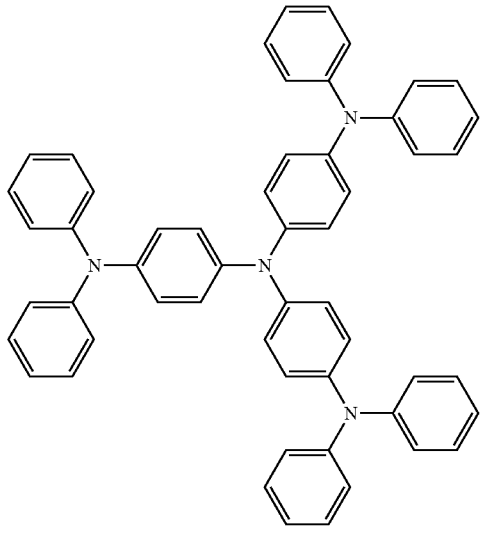

TDATA

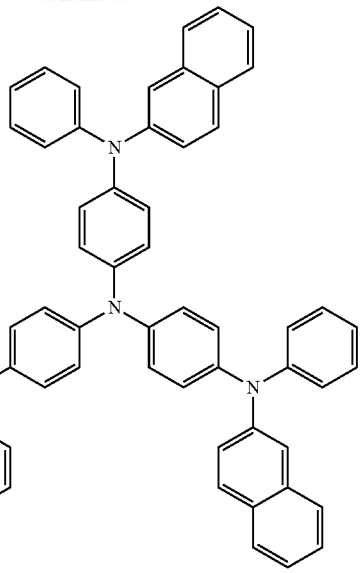

2-TNATA

The thickness of the HIL may be from about 100 Å to about 10000 Å, and in some embodiments, from about 100 Å to about 1000 Å. When the thickness of the HIL is within these ranges, the HIL may have good hole injecting ability without imparting a substantial increase in driving voltage to an OLED including it.

Then, a HTL may be formed on the HIL by using one of vacuum deposition, spin coating, casting, Langmuir-Blodgett (LB) deposition, and the like. When the HTL is formed using one of vacuum deposition and spin coating, the conditions for deposition and coating may be similar to those for the formation of the HIL, though the conditions for the deposition and coating may vary according to the material that is used to form the HTL.

The HTL may be formed of any known hole transporting materials. Non-limiting examples of suitable HTL forming materials are carbazole derivatives, such as N-phenylcarbazole or polyvinylcarbazole, N,N-bis(3-methylphenyl)-N,N-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB).

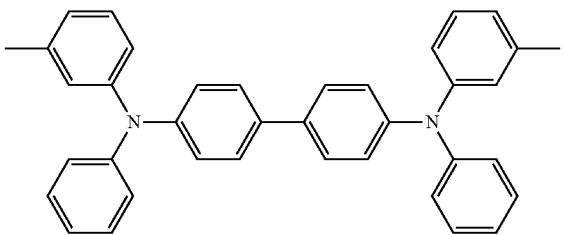

TPD

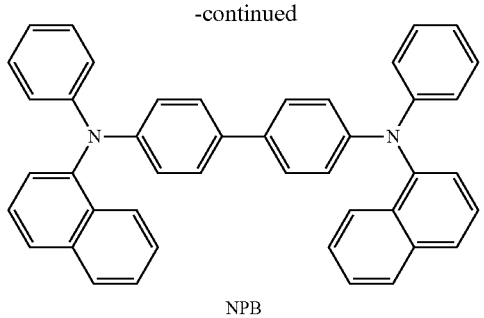

NPB

The thickness of the HTL may be from about 50 Å to about 2000 Å, and, in some embodiments, from about 100 Å to about 1500 Å. When the thickness of the HTL is within these ranges, the HTL may have good hole transporting ability without imparting a substantial increase in driving voltage to an OLED including it.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without imparting a substantial increase in driving voltage to an OLED including it.

In some embodiments, at least one of the HIL, HTL, and H-functional layer may include at least one of a compound of formula 300 below and a compound of Formula 350 below:

<Formula 300>

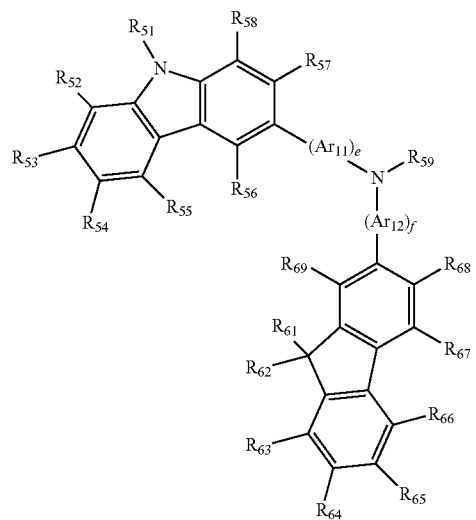

<Formula 350>

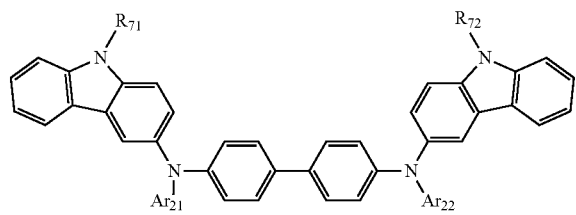

In Formulae 300 and 350, $Ar_{11}$, $Ar_{12}$, $Ar_{21}$, and $Ar_{22}$ may be each independently a substituted or unsubstituted $C_5$-$C_{60}$ arylene group.

In Formula 300, e and f may be each independently an integer of 0 to 5. For example, e and f in Formula 300 may be each independently 0, 1, or 2. In some other embodiments, e may be 1, and f may be zero, but they are not limited thereto.

In Formulae 300 and 350, $R_{51}$ to $R_{58}$, $R_{61}$ to $R_{69}$, $R_{71}$, and $R_{72}$ may be each independently one of a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, and a substituted or unsubstituted $C_5$-$C_{60}$ arylthio group. In some embodiments, $R_{51}$ to $R_{58}$, $R_{61}$ to $R_{69}$, $R_{71}$ and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group; a naphthyl group; an anthryl group; a biphenyl group; a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In some embodiments, the compound of Formula 300 above may be a compound represented by Formula 300A below, but it is not limited thereto:
<Formula 300A>
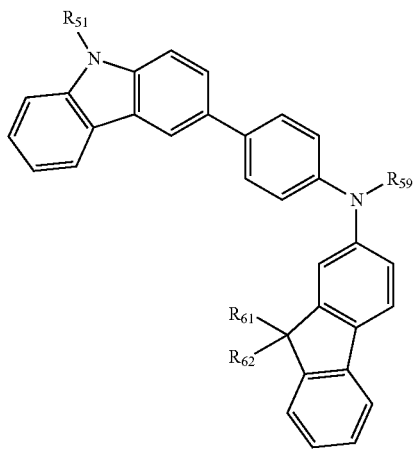
In Formula 300A, $R_{51}$, $R_{62}$ $R_{61}$, and $R_{59}$ are as defined above.
In some other embodiments, at least one of the HIL, HTL, and H-functional layer may include at least one of the compounds 301 to 320 below, but they are not limited thereto:
301
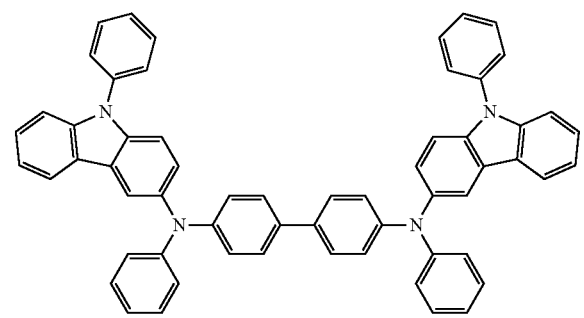
302
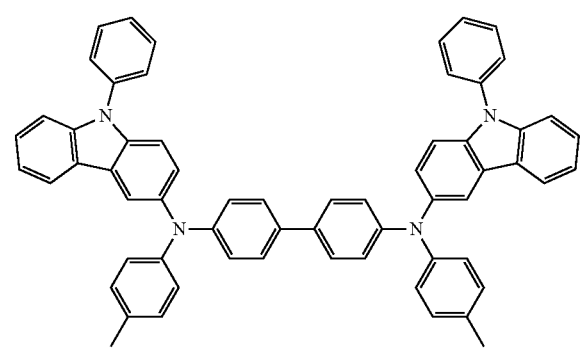
303
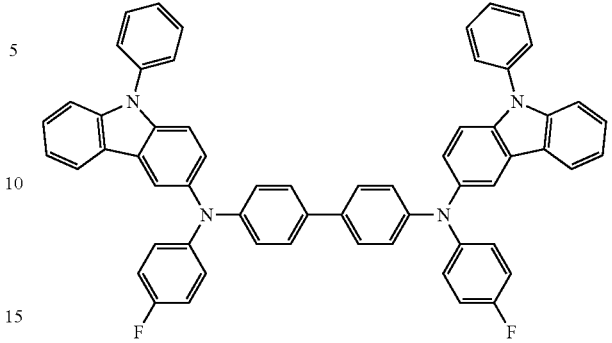
304
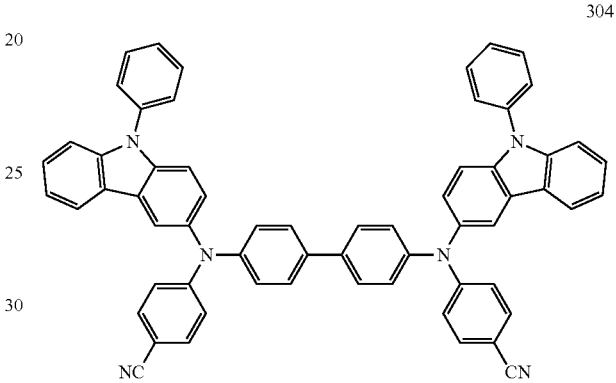
305
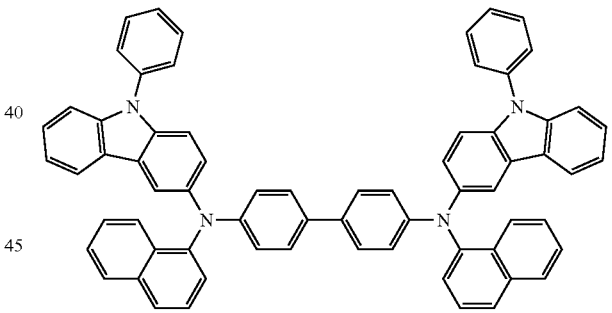
306
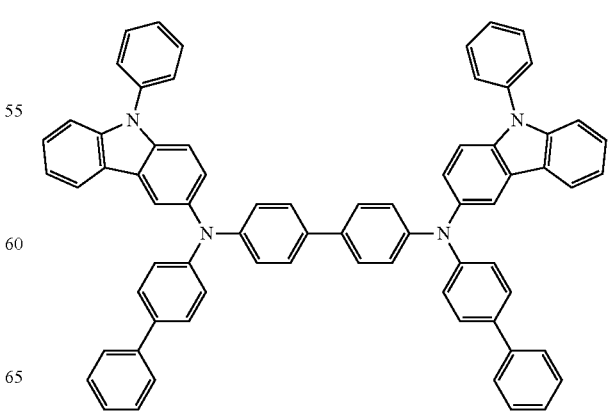

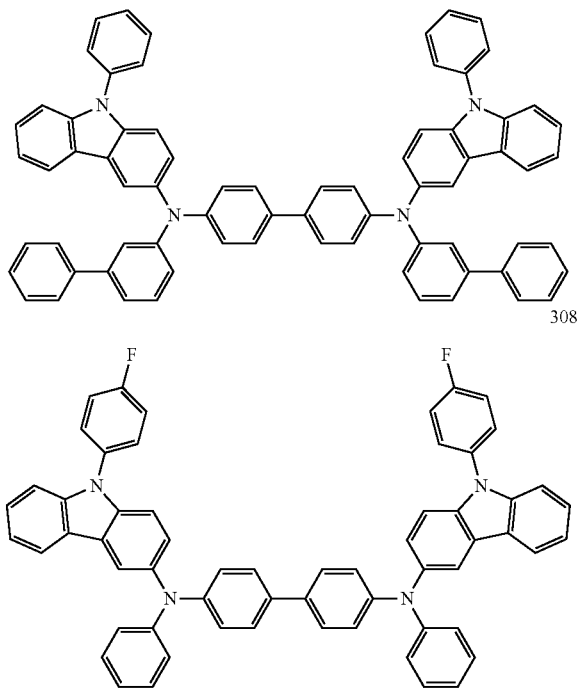

307

308

At least one of the HIL, HTL, and H-functional layer may further include a charge-generating material for improved layer conductivity, in addition to a hole injecting material, a hole transport material, and/or a material having both hole injection and hole transport capabilities as described above.

The charge-generating material may be, for example, a p-dopant. The p-dopant may be one of quinine derivatives, metal oxides, and compounds with a cyano group, but it is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-CTNQ), and the like; Metal oxides such as tungsten oxide, molybdenum oxide, and the like; and cyano-containing compounds such as Compound 200 below.

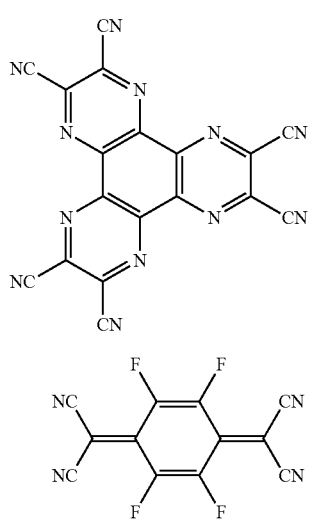

<Compound 200>

<F4-CTNQ>

When one of the hole injection layer, the hole transport layer, and the H-functional layer further includes a charge-generating material, the charge-generating material may be homogeneously dispersed or inhomogeneously distributed in the layer.

A buffer layer may be disposed between the EML and at least one of the HIL, HTL and H-functional layer. The buffer layer may compensate for an optical resonance distance of light according to a wavelength of the light emitted from the EML, and thus may increase efficiency. The buffer layer may include one of any hole injecting material and any hole transporting material. In some other embodiments, the buffer layer may include the same material as one of the materials included in the at least one of a HIL, a HTL, and a H-functional layer that underly the buffer layer.

Then, an EML may be formed on one of the HTL, the H-functional layer, and the buffer layer by one of vacuum deposition, spin coating, casting, Langmuir-Blodget (LB) deposition, and the like. When the EML is formed using one of vacuum deposition and spin coating, the deposition and coating conditions may be similar to those for the formation of the HIL, though the conditions for deposition and coating may vary according to the material that is used to form the EML.

The EML may include the heterocyclic compound of Formula 1 above and any of a variety of known light-emitting materials. In some embodiments, the EML may also be formed using a known host and a dopant. Dopants that may be used to form the EML may include either a fluorescent dopant or a phosphorescent dopant. Non-limiting examples of known hosts are tris(8-hydroxyquinolinato) aluminum (Alq$_3$), 4,4'-N,N'-dicarbazole-biphenyl (CBP), poly(n-vinylcarbazole) (PVK), 9,10-di(naphthalene-2-yl) anthracene (ADN), TCTA, 1,3,5-tris(N-phenylbenzimidazole-2-yl)benzene (TPBI), 3-tert-butyl-9,10-di-2-naphthylanthracene (TBADN), 2,7-bis(9,9-diethylfluoren-2-yl)-9, 9-diethylfluorene (E3), distyrylarylene (DSA), 2,2'-dimethyl-4,4'-bis(N-carbazolyl)biphenyl (dmCBP) and Compounds 501 to 509 below.

TPBI

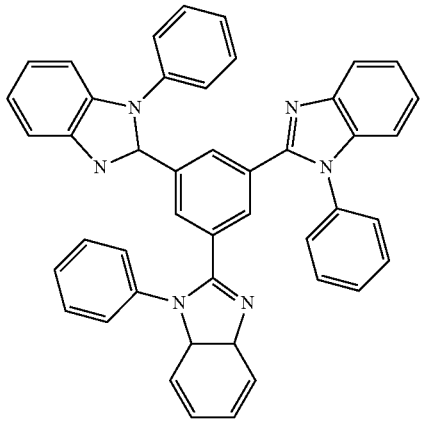

TBADN

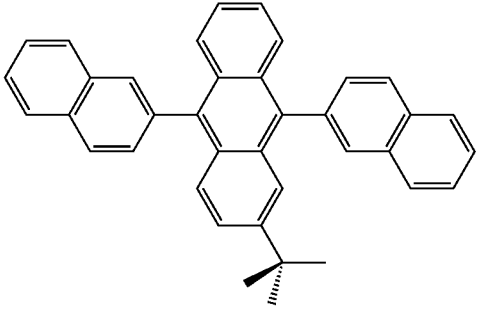

E3
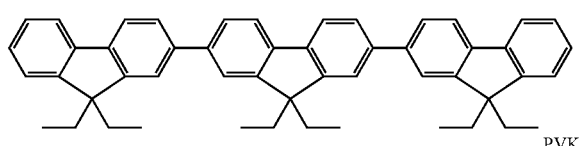
PVK
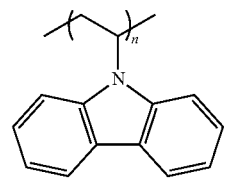
ADN
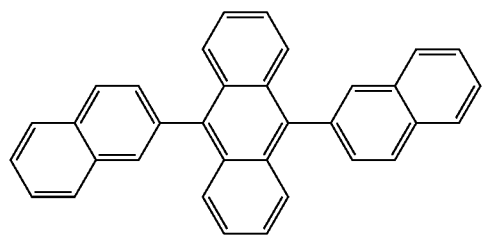
CBP
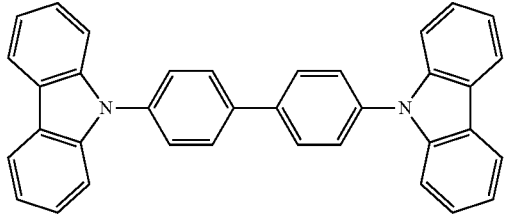
dmCBP
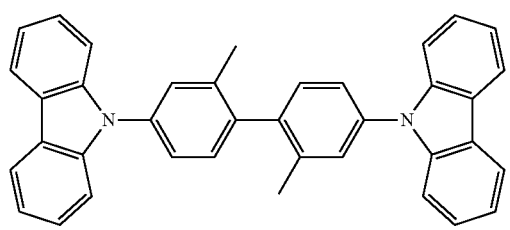
501
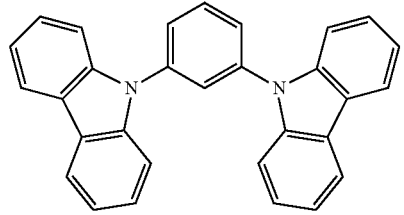
502
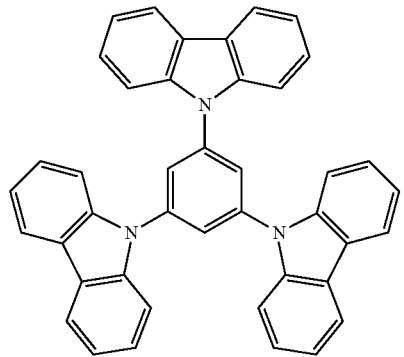
503
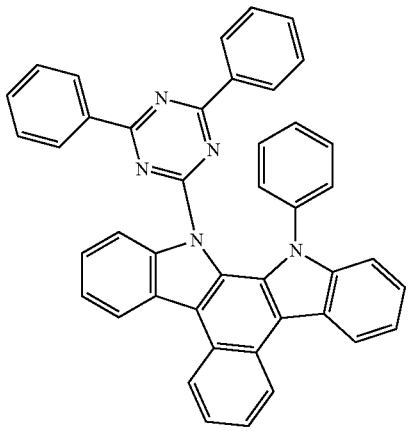
504
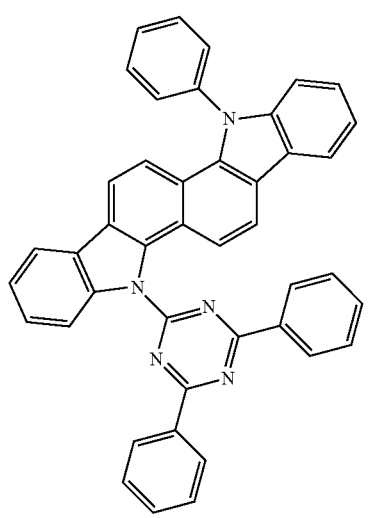
505
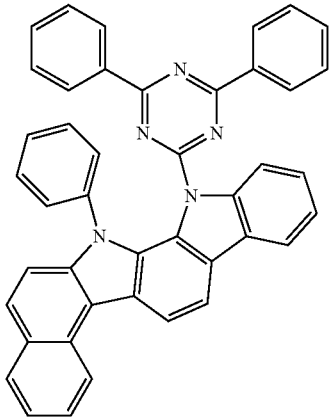

-continued

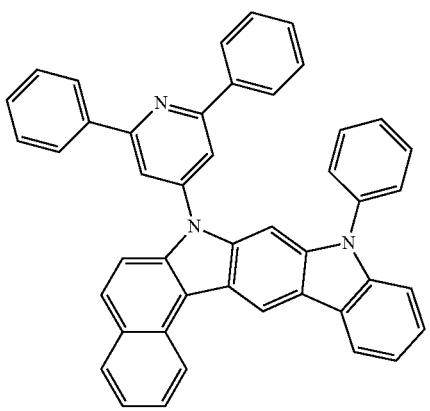
506

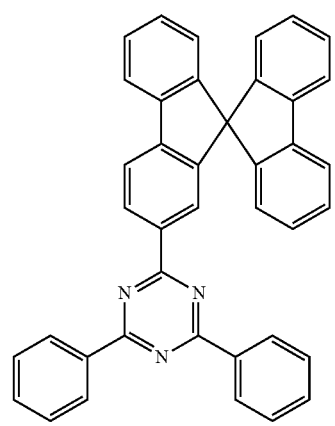
507

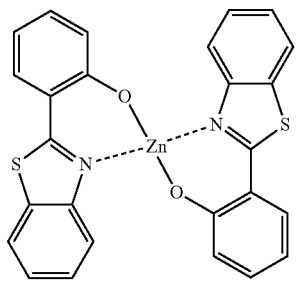
508

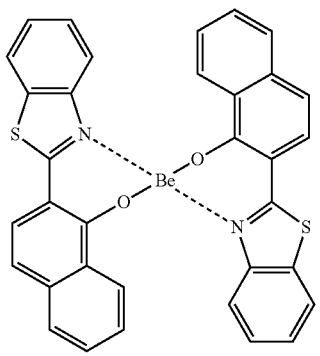
509

In some embodiments, an anthracene-based compound represented by Formula 400 below may be used as the host.

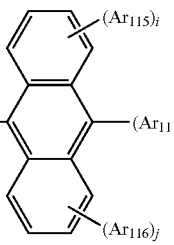

<Formula 400>

In Formula 400, $Ar_{111}$ and $Ar_{112}$ may be each independently a substituted or unsubstituted $C_5$-$C_{60}$ arylene group; $Ar_{113}$ to $Ar_{116}$ may be each independently one of a substituted or unsubstituted $C_1$-$C_{10}$ alkyl group and a substituted or unsubstituted $C_5$-$C_{60}$ aryl group; and g, h, i, and j are each independently an integer from 0 to 4.

In some embodiments, $Ar_{111}$ and $Ar_{112}$ in Formula 400 may be each independently one of a phenylene group, a naphthylene group, a phenanthrenylene group, and a pyrenylene group; and a phenylene group, a naphthylene group, a phenanthrenylene group, a fluorenyl group, and a pyrenylene group that are substituted with at least one of a phenyl group, a naphthyl group, and an anthryl group, but they are not limited thereto.

In Formula 400 above, g, h, i, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group, but they are not limited thereto.

For example, the anthracene compound of Formula 400 above may be one of the compounds represented by the following formulae, but it is not limited thereto:

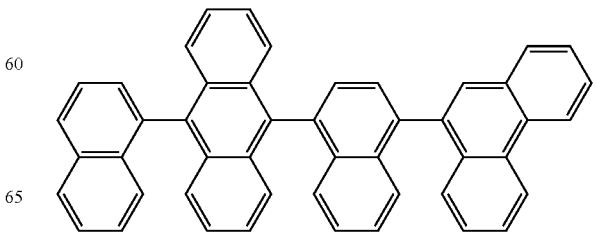

-continued
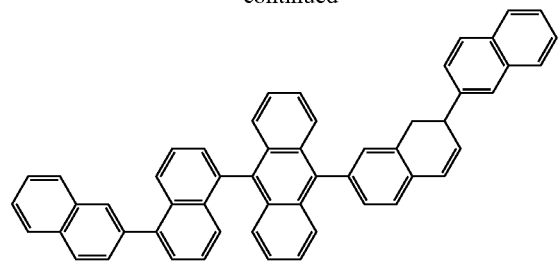
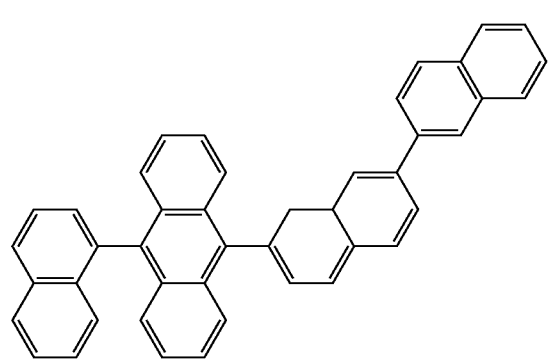
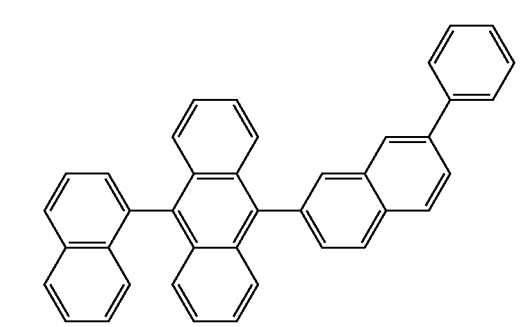
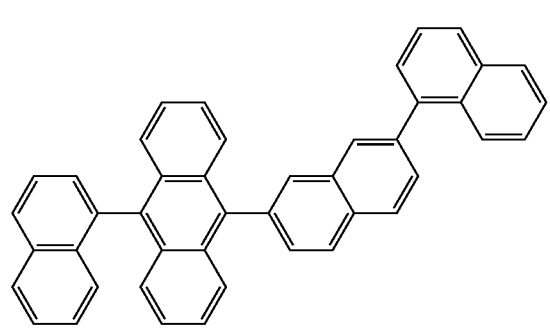
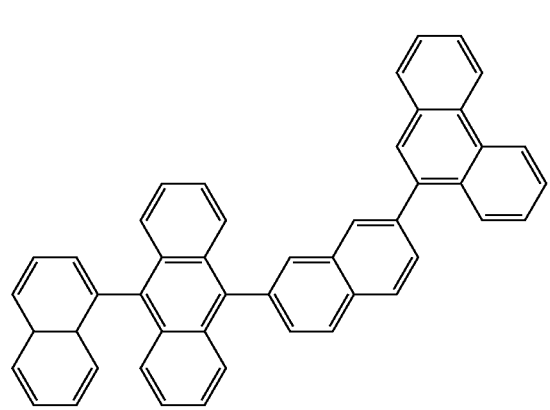
-continued
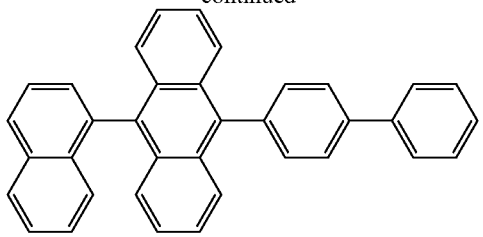
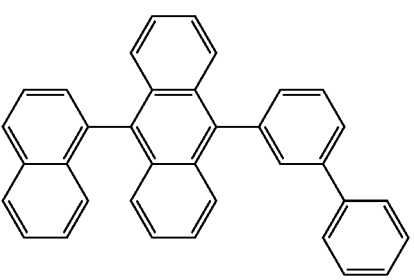
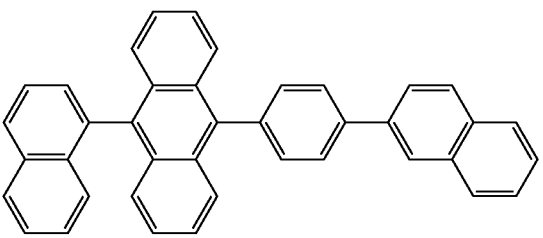
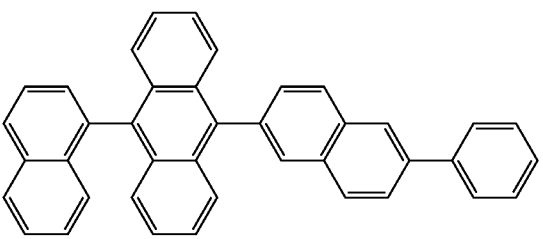
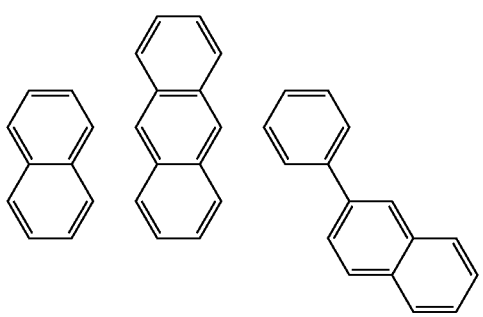
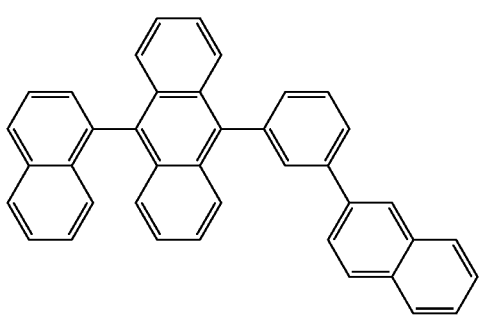

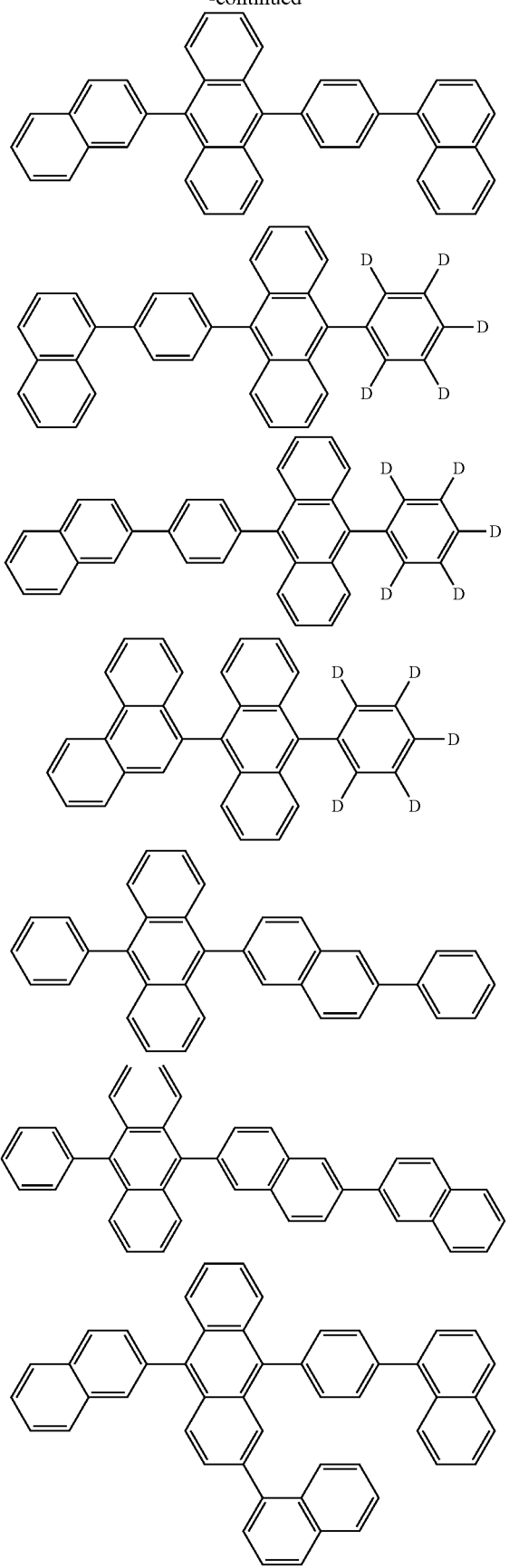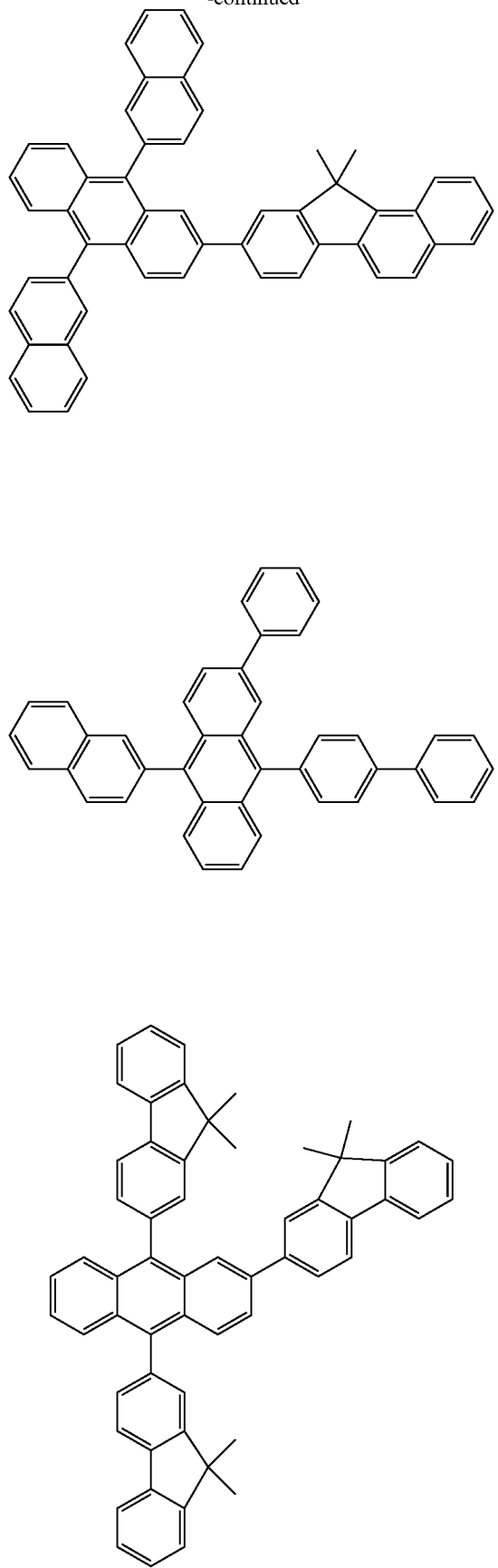

-continued

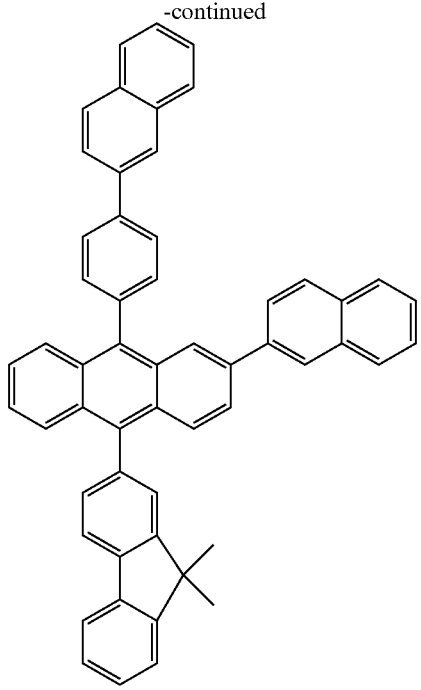

In some embodiments, an anthracene-based compound represented by Formula 401 below may be used as the host.

Formula 401

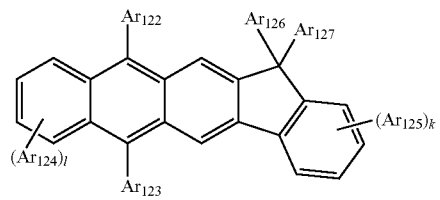

$Ar_{122}$ to $Ar_{125}$ in Formula 401 above may be as defined above in conjunction with $Ar_{113}$ of Formula 400, and thus detailed descriptions thereof will not be provided here.

$Ar_{126}$ and $Ar_{127}$ in Formula 401 above may be each independently a $C_1$-$C_{10}$ alkyl group, for example, one of a methyl group, an ethyl group, and a propyl group.

In Formula 401, k and l may be each independently an integer from 0 to 4, for example, 0, 1, or 2.

For example, the anthracene compound of Formula 401 above may be one of the compounds represented by the following formulae, but it is not limited thereto:

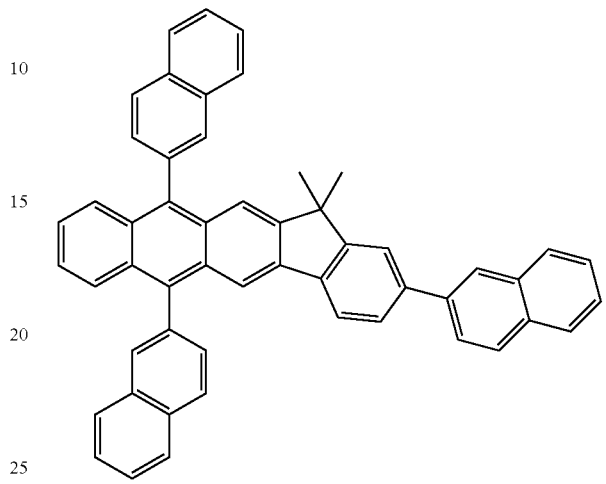

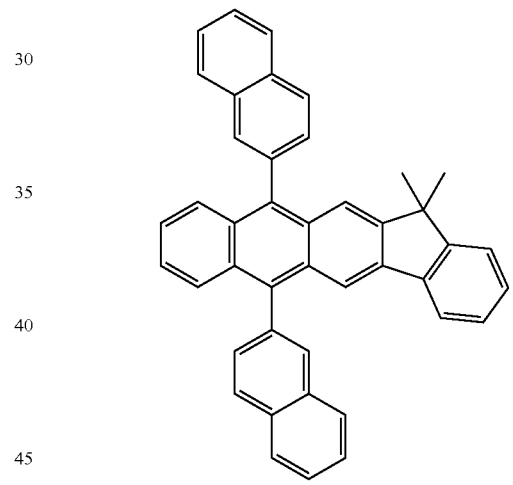

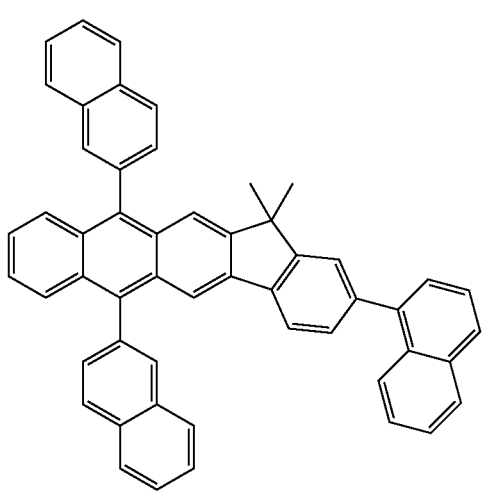

-continued

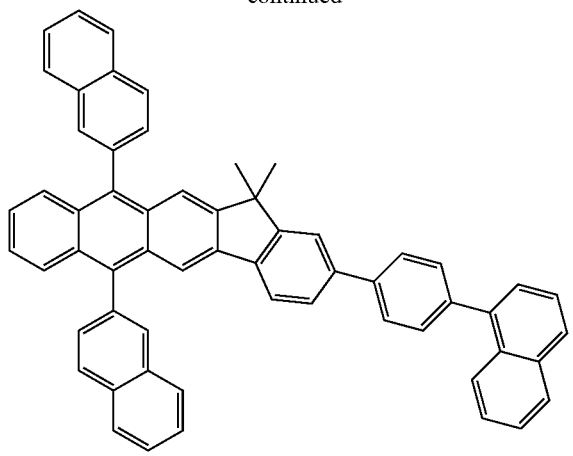

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Non-limiting examples of the blue dopant are compounds represented by the following formulae.

F$_2$Irpic

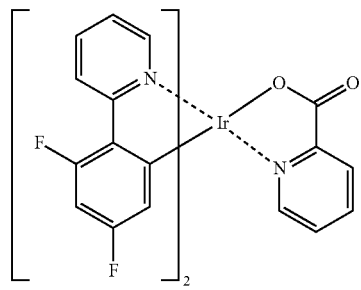

(F$_2$ppy)$_2$Ir(tmd)

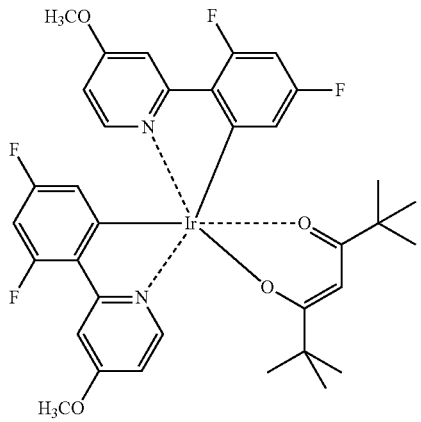

Ir(dfppz)$_3$

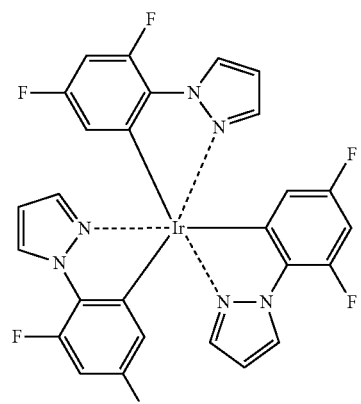

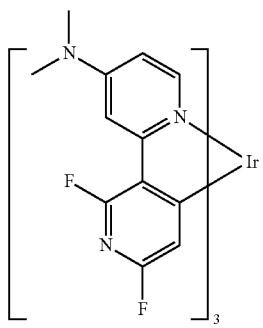

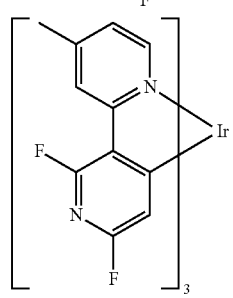

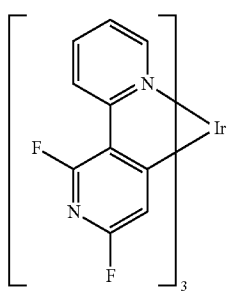

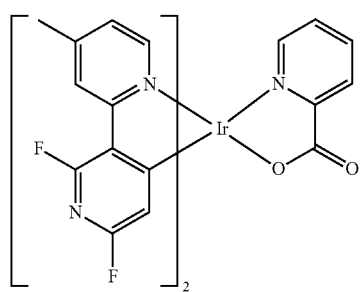
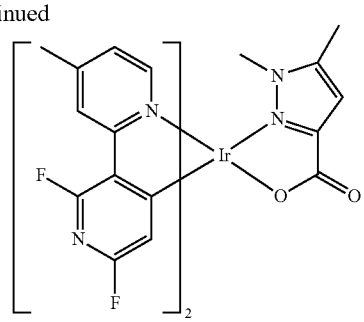
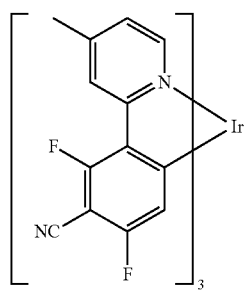
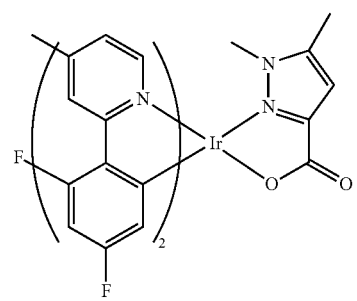
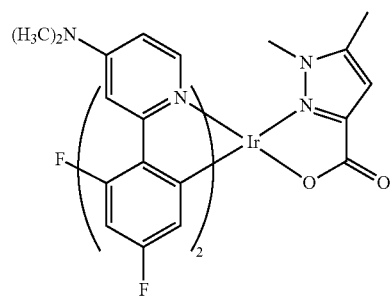
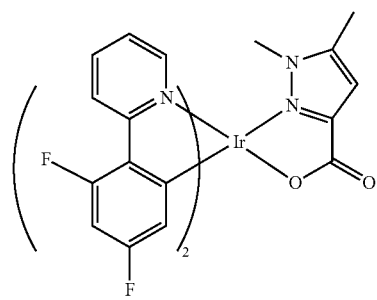
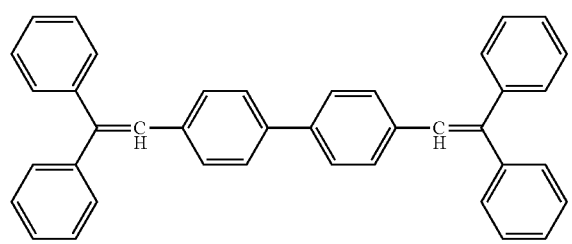
DPVBI
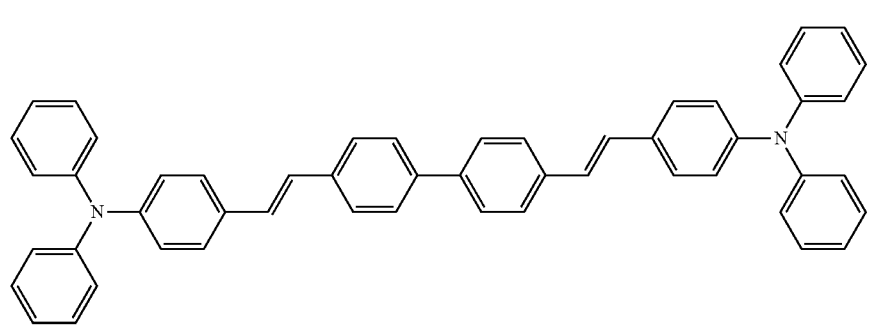
DPAVBi

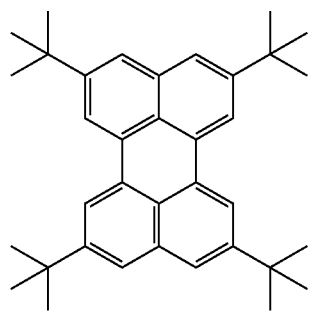
TBPe
Non-limiting examples of the red dopant are compounds represented by the following formulae.
PtOEP
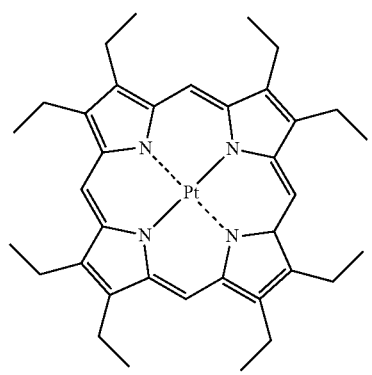
Ir(pq)₂(acac)
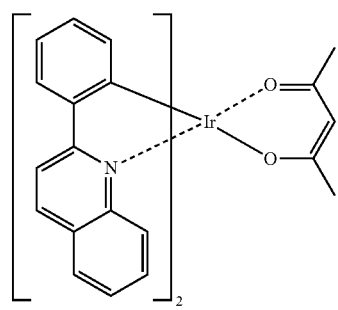
Ir(pig)₃
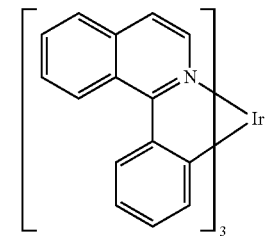
Ir(2-phq)₃
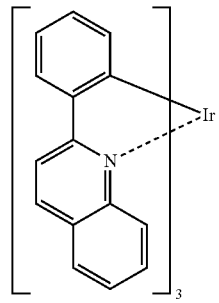
Btp₂Ir(acac)
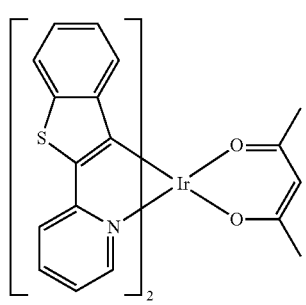
Ir(BT)₂(acac)
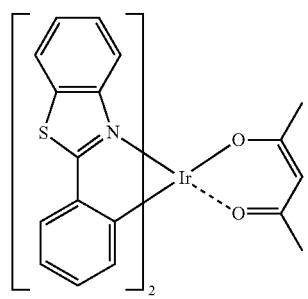
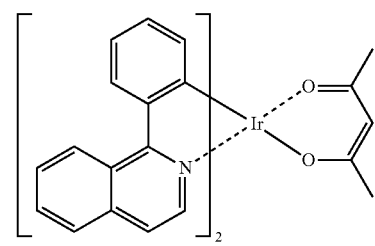

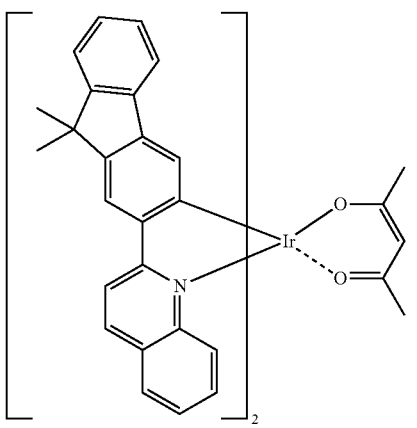
(Ir(flq)₂(acac))
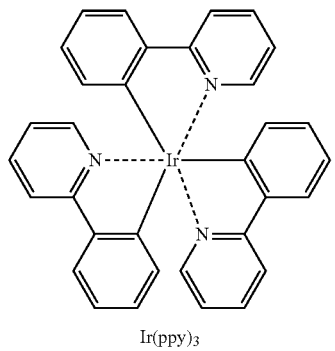
Ir(ppy)₃
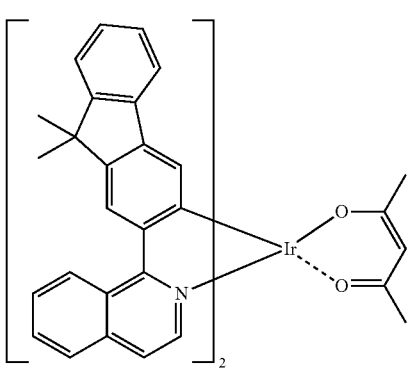
Ir(fliq)₂(acac)
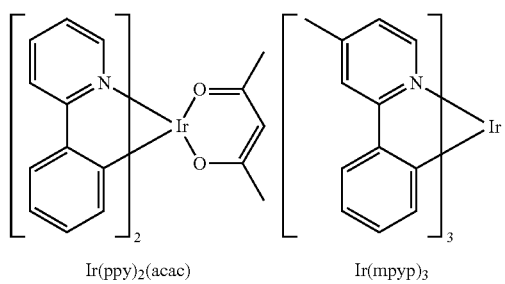
Ir(ppy)₂(acac)   Ir(mpyp)₃
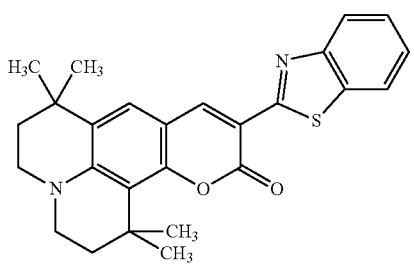
C545T
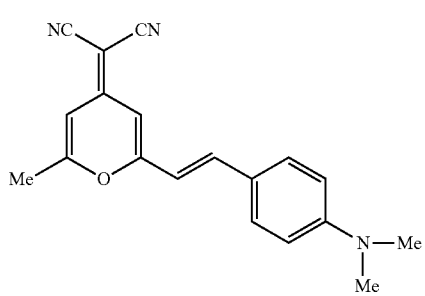
DCM
Non-limiting examples of the dopant that may be used in the EML are Pt complexes represented by the following formulae.
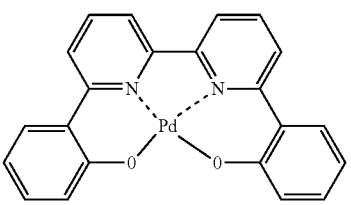
D1
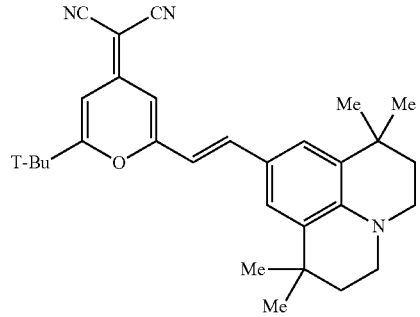
DCJTB
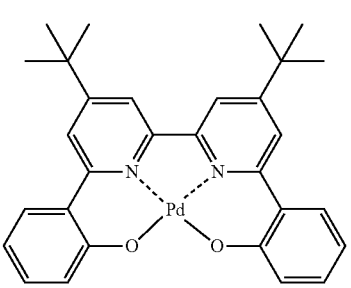
D2
Non-limiting examples of the green dopant are compounds represented by the following formulae.

D3
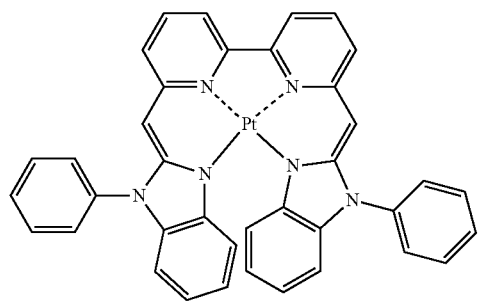
D4
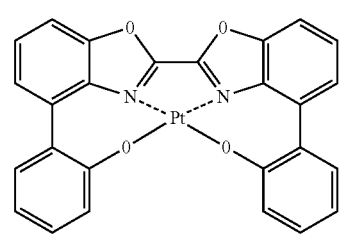
D5
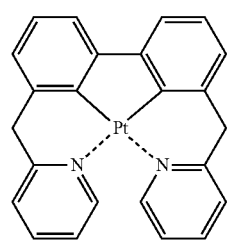
D6
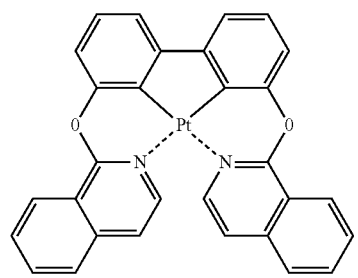
D7
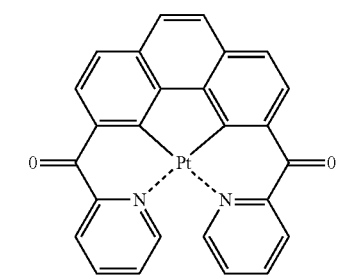
D8
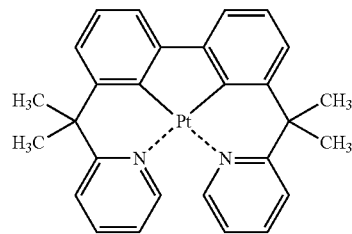
D9
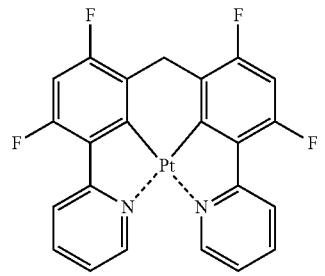
D10
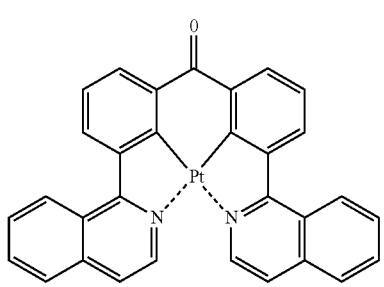
D11
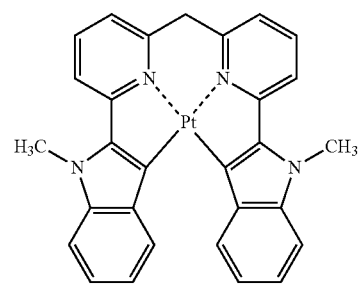
D12
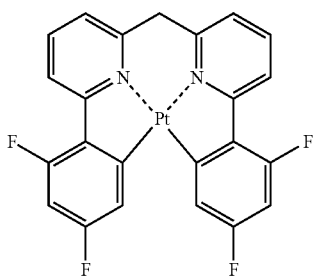
D13
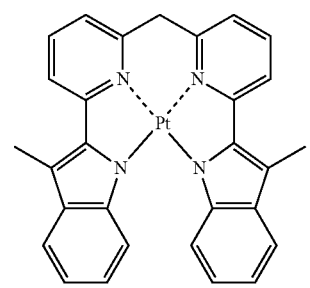

D14
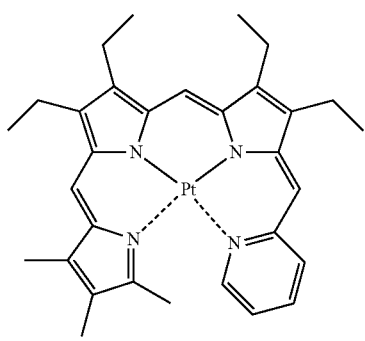
D15
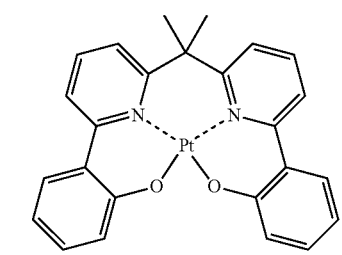
D16
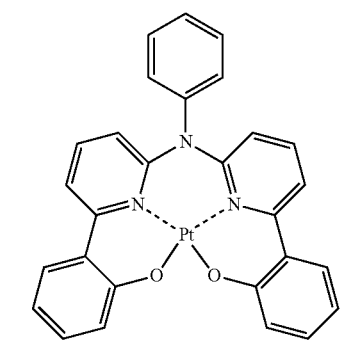
D17
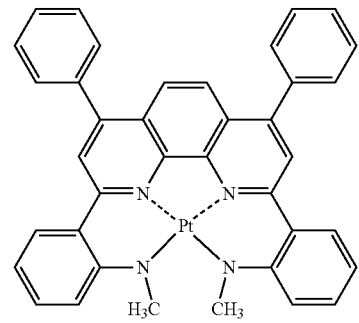
D18
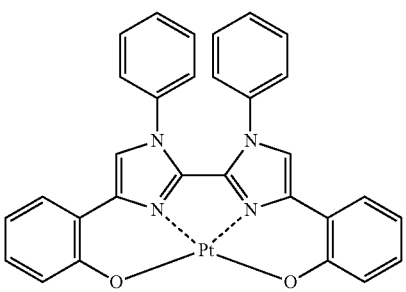
D19
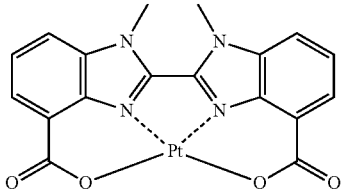
D20
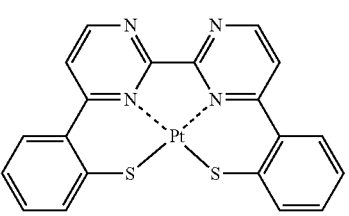
D21
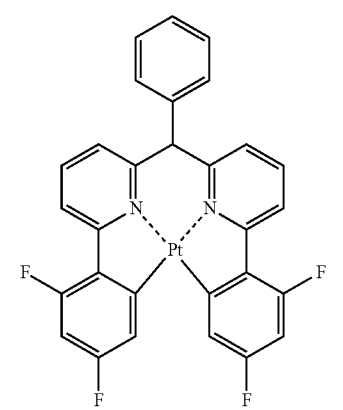
D22
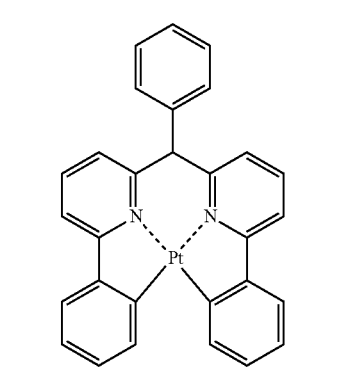
D23
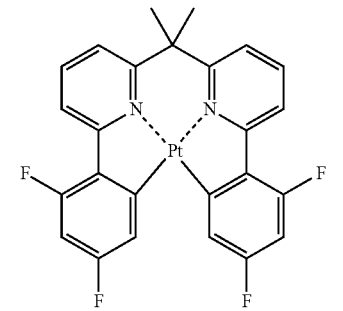

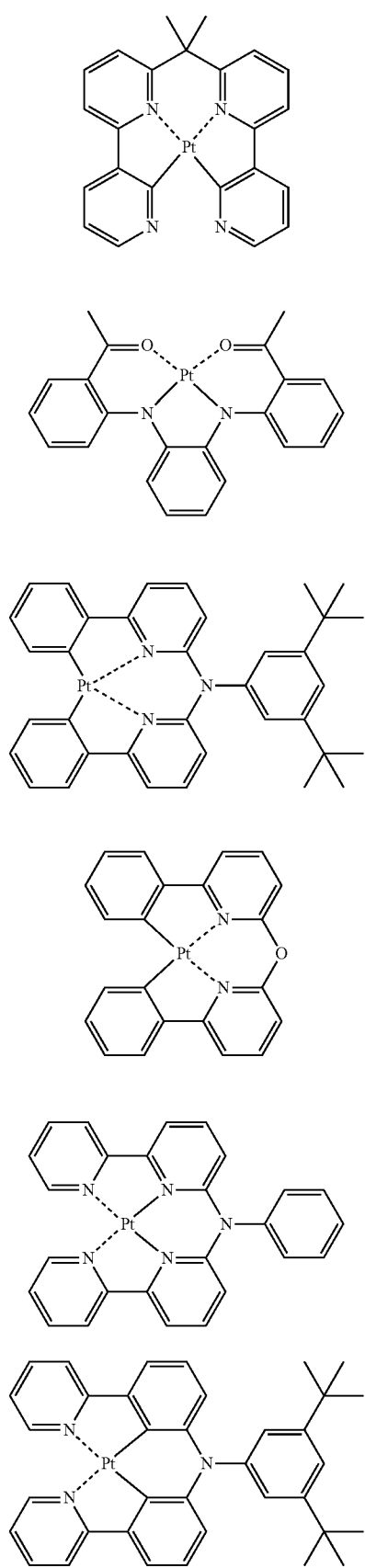
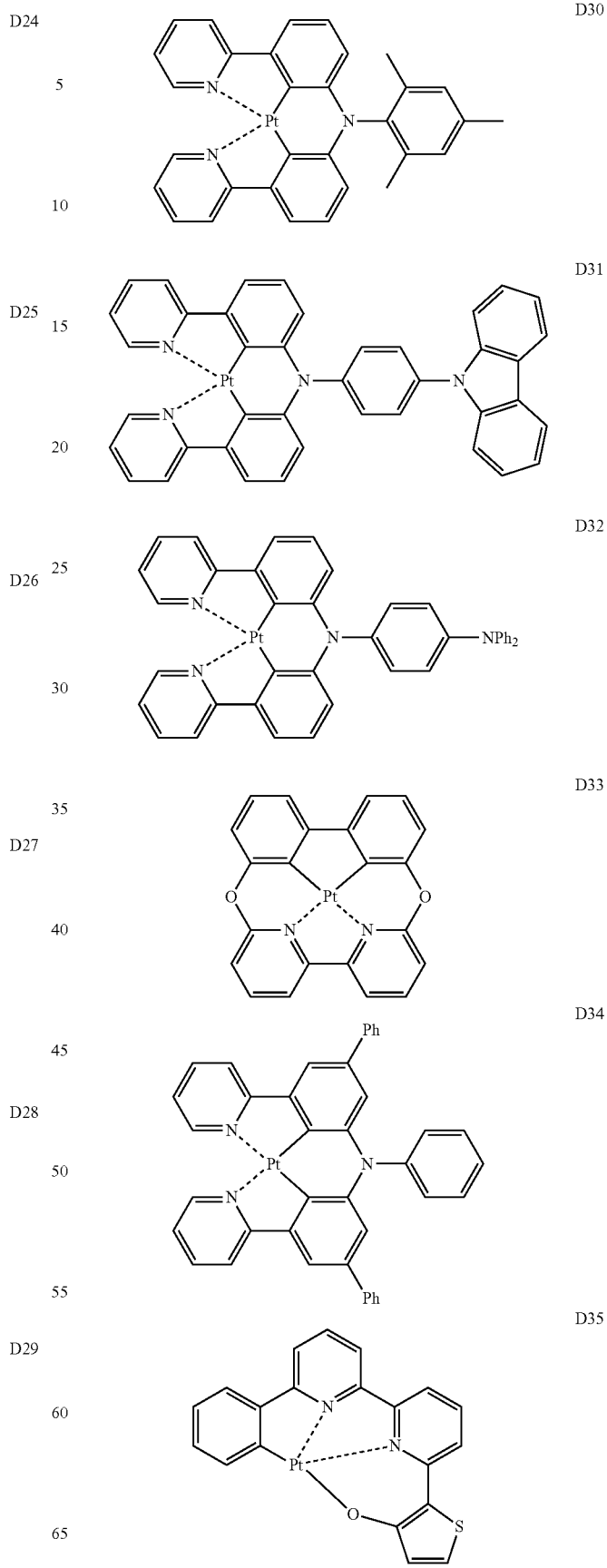

D36 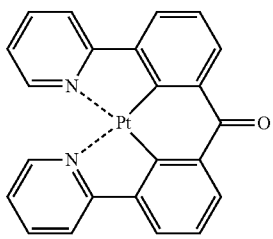
D37 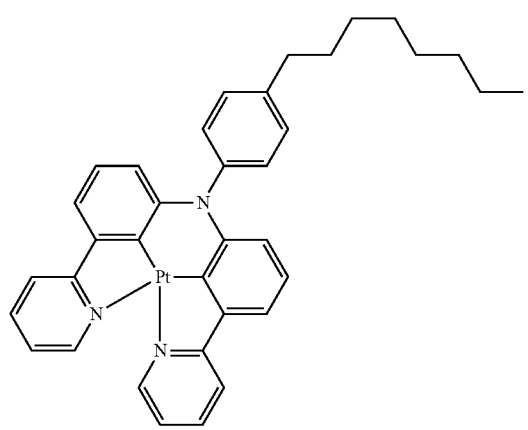
D38 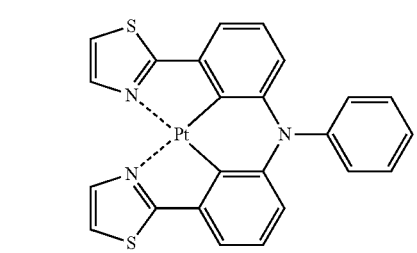
D39 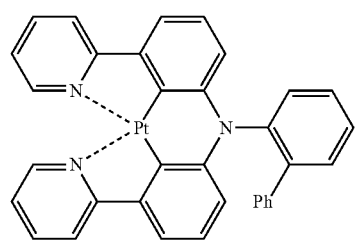
D40 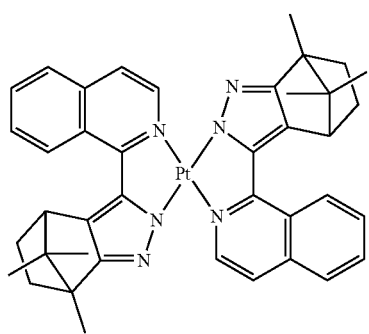
D41 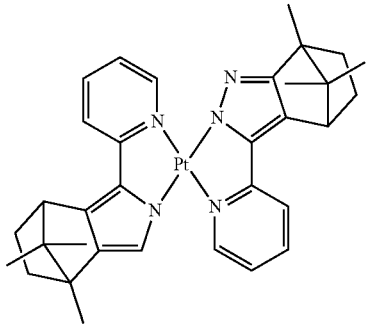
D42 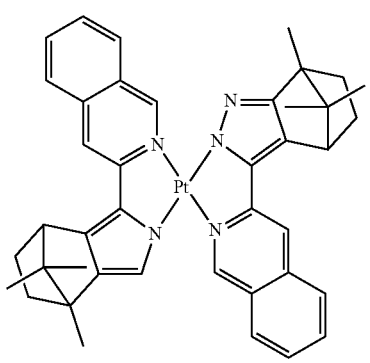
D43 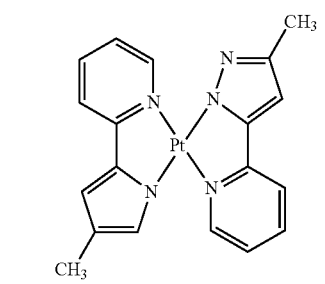
D44 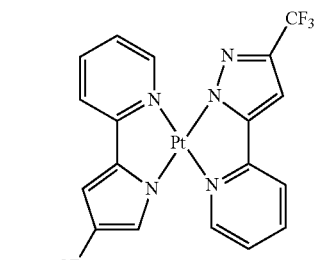
D45 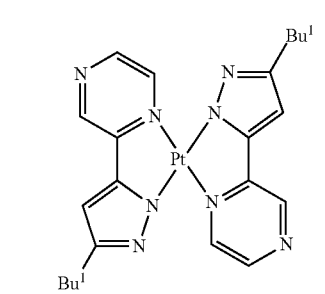

Non-limiting examples of the dopant that may be used in the EML are Os complexes represented by the following formulae.

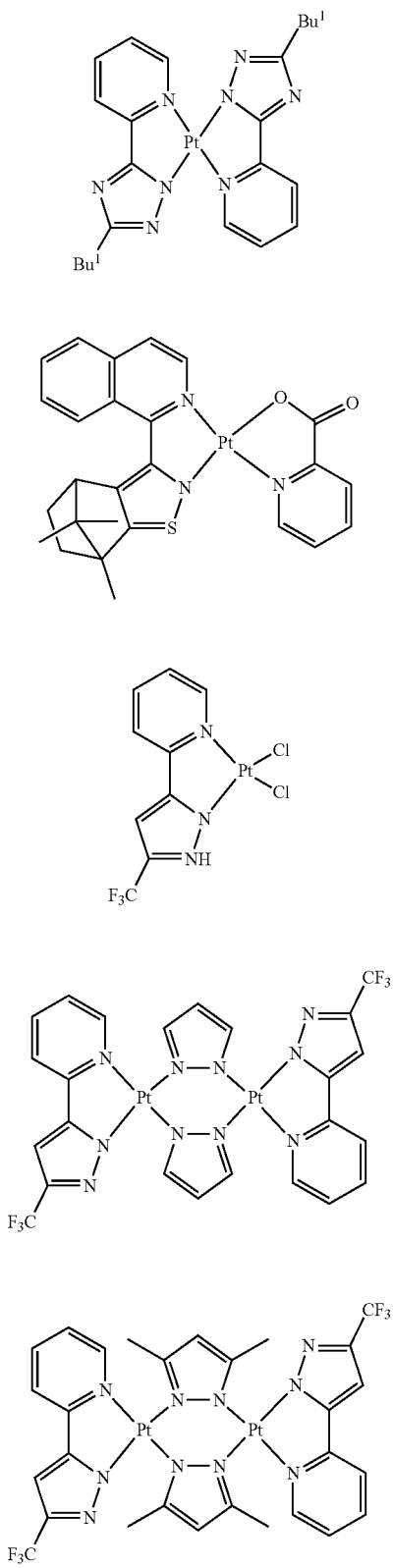
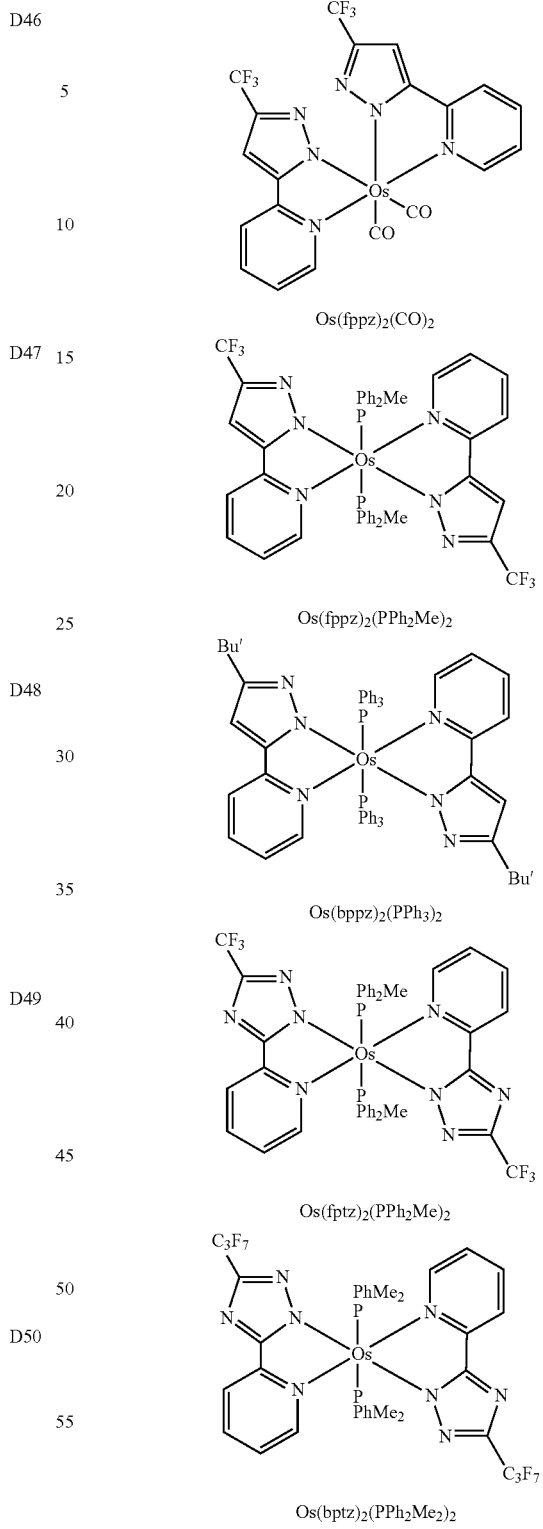

Os(fppz)₂(CO)₂

Os(fppz)₂(PPh₂Me)₂

Os(bppz)₂(PPh₃)₂

Os(fptz)₂(PPh₂Me)₂

Os(bptz)₂(PPh₂Me₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and, in some embodiments, from about 200

Å to about 600 Å. When the thickness of the EML is within these ranges, the EML may have good light emitting ability without imparting a substantial increase in driving voltage to an OLED that includes it.

Then, an ETL may be formed on the EML by one of vacuum deposition, spin coating, casting, and the like. When the ETL is formed using one of vacuum deposition and spin coating, the deposition and coating conditions may be similar to those for the formation of the HIL, though the deposition and coating conditions may vary according to a compound that is used to form the ETL. A material for forming the ETL may be any material that can stably transport electrons injected from an electron injecting electrode (cathode). Non-limiting examples of materials useful for forming the ETL are a quinoline derivative, such as tris(8-quinolinorate)aluminum (Alq3), 3-(4-biphenyl)-4-phenyl-5-[4-(tert-butyl)phenyl]-1,2,4-triazole (TAZ), BAlq, beryllium bis(benzoquinolin-10-olate) (Bebq$_2$), 9,10-di(naphthalene-2-yl)anthracene (ADN), Compound 201, and Compound 202, but they are not limited thereto.

TAZ

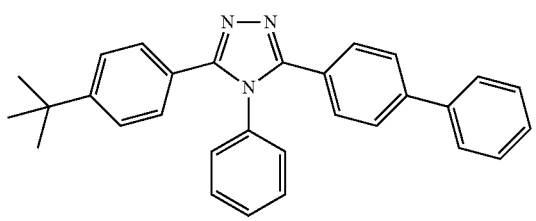

BAlq

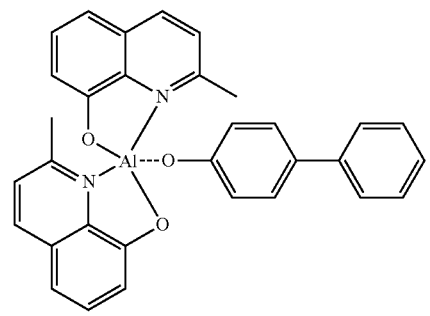

<Compound 201>

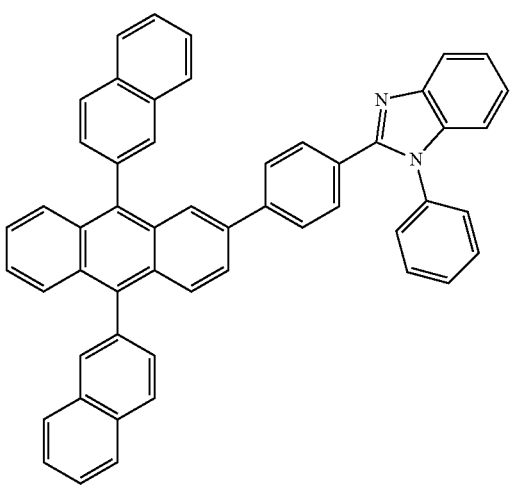

<Compound 202>

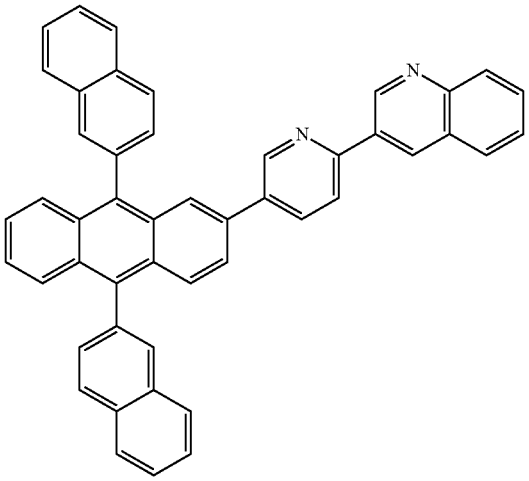

BCP

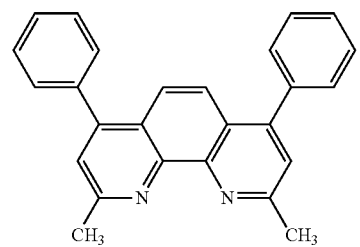

The thickness of the ETL may be from about 100 Å to about 1000 Å, and, in some embodiments, from about 150 Å to about 500 Å. When the thickness of the ETL is within these ranges, the ETL may have satisfactory electron transporting ability without imparting a substantial increase in driving voltage to an OLED that includes it.

In some embodiments, the ETL may further include a metal-containing material, in addition to an electron-transporting organic compound.

The metal-containing material may include a lithium (Li) complex. Non-limiting examples of the Li complex are lithium quinolate (LiQ) and Compound 203 below:

<Compound 203>

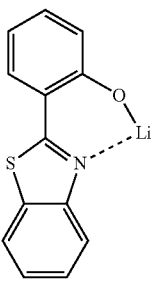

Then, an EIL, which facilitates injection of electrons from the cathode, may be formed on the ETL. Any suitable electron-injecting material may be used to form the EIL.

Non-limiting examples of materials useful for forming the EIL are LiF, NaCl, CsF, Li$_2$O, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and, in some embodiments, from about 3 Å to about 90 Å. When the thickness of the EIL is within these ranges, the EIL may have satisfactory electron injection ability without imparting a substantial increase in driving voltage to an OLED that includes it.

Finally, the second electrode is disposed on the organic layer. The second electrode may be a cathode that is an electron injection electrode. A material useful for forming the second electrode may be one of a metal, an alloy, an electro-conductive compound that has a low work function and a mixture thereof. In this regard, the second electrode may be formed of one of lithium (Li), magnesium (Mg), aluminum (Al), aluminum (Al)-lithium (Li), calcium (Ca), magnesium (Mg)-indium (In), magnesium (Mg)-silver (Ag) and the like and may be formed as a thin film type transmission electrode. In some embodiments, to manufacture a top-emission light-emitting device, the transmission electrode may be formed of one of indium tin oxide (ITO) and indium zinc oxide (IZO).

Although the organic light-emitting device of the FIGURE is described above, the present invention is not limited thereto.

When a phosphorescent dopant is used in the EML, a hole blocking layer (HBL) may be formed between the HTL and the EML or between the H-functional layer and the EML by using one of vacuum deposition, spin coating, casting, Langmuir-Blodgett (LB) deposition, and the like, in order to prevent diffusion of triplet excitons or holes into the ETL. When the HBL is formed using one of vacuum deposition and spin coating, the conditions for deposition and coating may be similar to those for the formation of the HIL, although the conditions for deposition and coating may vary according to the material that is used to form the HBL. Non-limiting examples of hole-blocking materials that may be used in the HBL are oxadiazole derivatives, triazole derivatives and phenanthroline derivatives. For example, bathocuproine (BCP), represented by the following formula, may be used as a material for forming the HBL.

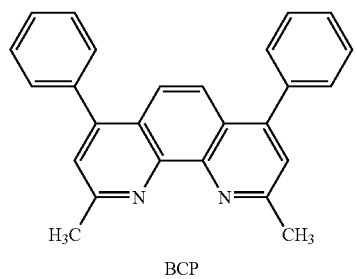 [SMILES: Cc1cc(-c2ccccc2)c2ccc3c(-c4ccccc4)cc(C)nc3c2n1 ; "BCP"]

BCP

The thickness of the HBL may be from about 20 Å to about 1000 Å, and, in some embodiments, from about 30 Å to about 300 Å. When the thickness of the HBL is within these ranges, the HBL may have improved hole blocking ability without imparting a substantial increase in driving voltage to an OLED that includes it.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments, the organic layer of the organic light-emitting device may be formed of the compound of Formula 1 by using a deposition method, or it may be formed using a wet method of coating a solution of the compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1

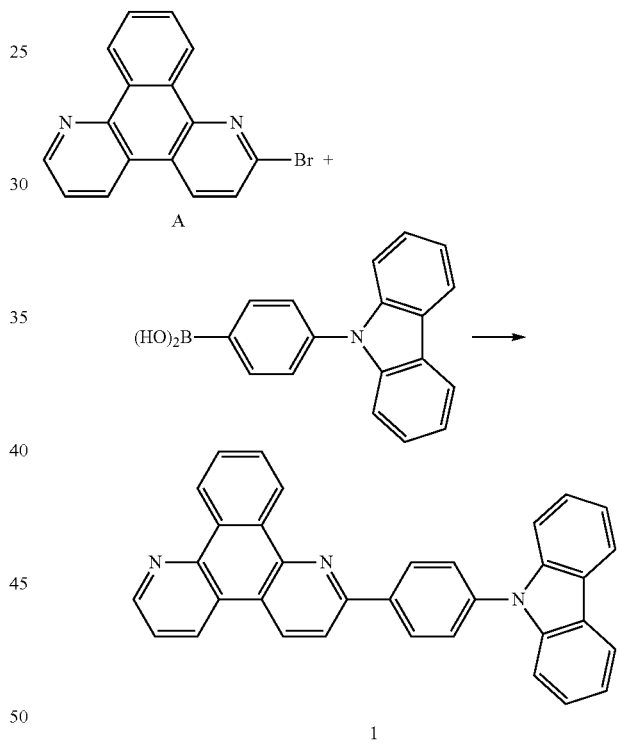

Synthesis of Compound 1

A quantity of 10 g (1 eq, 0.044 mol) of Intermediate A, and 14.06 g (1.1 eq, 0.049 mol) 4-(9H-carbazol-9-yl)phenylboronic acid were dissolved with 700 ml of toluene in a flask. A quantity of 0.92 g (0.02 eq, 0.0008 mmol) of Pd(PPh$_3$)$_4$ and 30 mL of a 2M K$_2$CO$_3$ solution were added into the solution, then heated while stirring for about 12 hours. When reaction was complete, the reaction solution was filtered through Celite, and a filtered product was refined by column chromatography to obtain 14.7 g of Compound 1 with a yield of about 84.2%.

Elemental Analysis for C$_{34}$H$_{21}$N$_3$: calcd C, 86.60; H, 4.49; N, 8.91.

HRMS for C$_{34}$H$_{21}$N$_3$ [M]+: calcd 471, found 471.

Synthesis Example 2

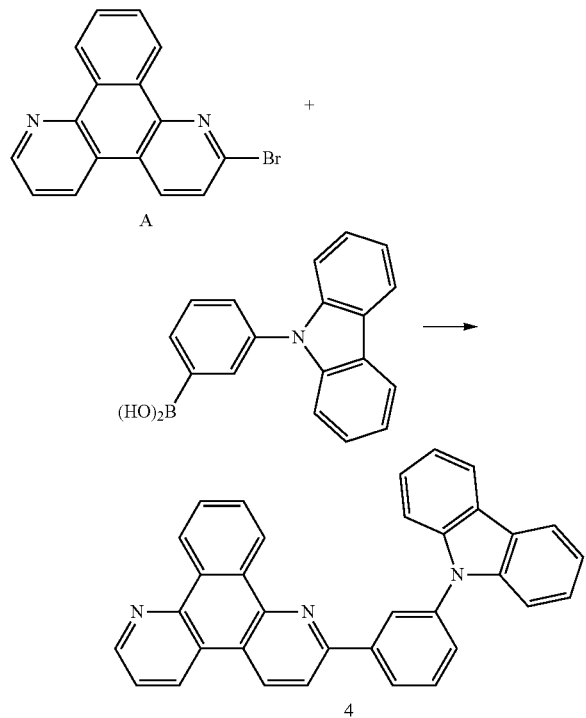

Synthesis of Compound 4

A quantity of 14.1 g of Compound 4 was synthesized with a yield of about 83.7% in the same manner as in Synthesis Example 1, except that 3-(9H-carbazol-9-yl)phenylboronic acid, instead of 4-(9H-carbazol-9-yl)phenylboronic acid, was used.

Elemental Analysis for C34H21N3: calcd C, 86.60; H, 4.49; N, 8.91.

HRMS for C34H21N3 [M]+: calcd 471, found 471.

Synthesis Example 3

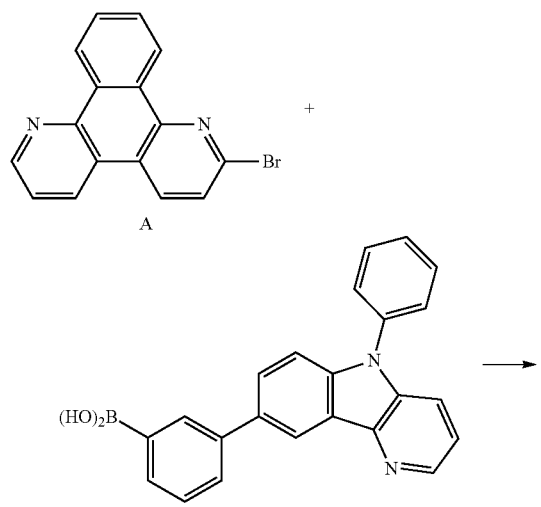

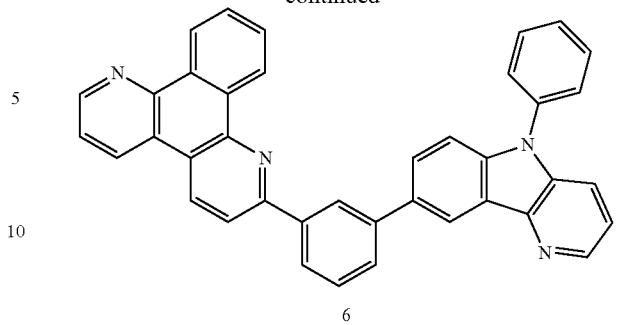

Synthesis of Compound 6

A quantity of 16.4 g of Compound 6 was synthesized with a yield of about 86.4% in the same manner as in Synthesis Example 1, except that 3-(5-phenyl-5H-pyrido[3,2-b]indol-8-yl)phenylboronic acid, instead of 4-(9H-carbazol-9-yl)phenylboronic acid, was used.

Elemental Analysis for C39H24N4: calcd C, 85.38; H, 4.41; N, 10.21.

HRMS for C39H24N4 [M]+: calcd 584, found 584.

Synthesis Example 4

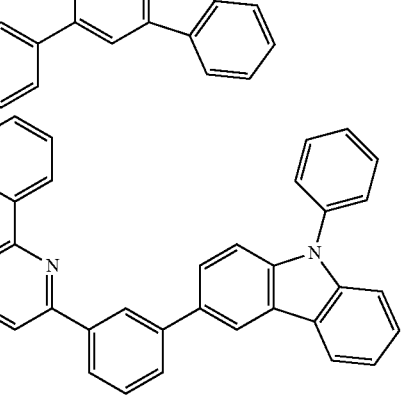

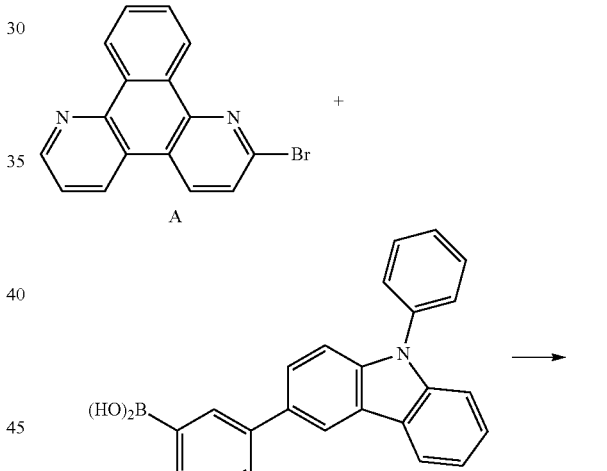

Synthesis of Compound 9

A quantity of 15.8 g of Compound 9 was synthesized with a yield of about 85.9% in the same manner as in Synthesis Example 1, except that 3-(9-phenyl-9H-carbazol-3-yl)phenylboronic acid, instead of 4-(9H-carbazol-9-yl)phenylboronic acid, was used.

Elemental Analysis for C40H25N3: calcd C, 87.73; H, 4.60; N, 7.67.

HRMS for C40H25N3 [M]+: calcd 547, found 547.

Synthesis Example 5

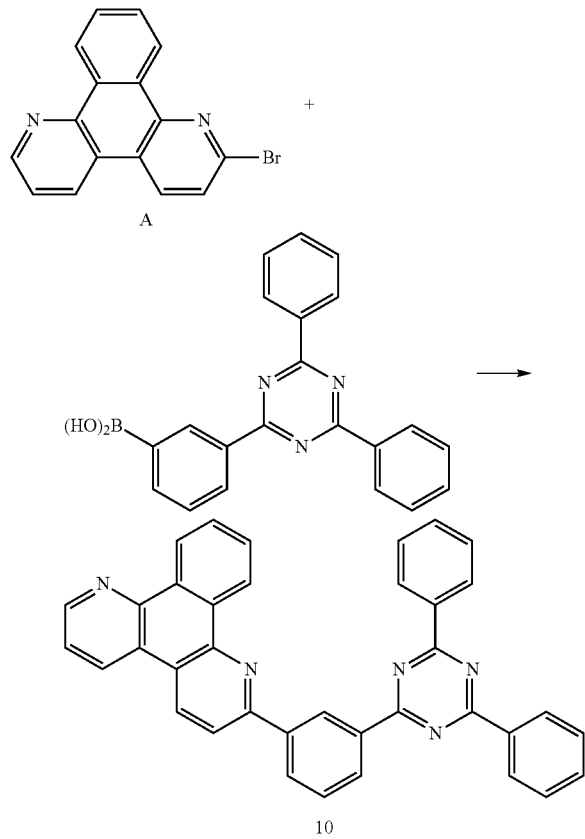

Synthesis of Compound 10

A quantity of 17.1 g of Compound 10 was synthesized with a yield of about 83.5% in the same manner as in Synthesis Example 1, except that 3-(4,6-diphenyl-1,3,5-triazin-2-yl)phenylboronic acid, instead of 4-(9H-carbazol-9-yl)phenylboronic acid, was used.

Elemental Analysis for C37H23N5: calcd C, 82.66; H, 4.31; N, 13.03.

HRMS for C37H23N5 [M]+: calcd 537, found 537.

Synthesis Example 6

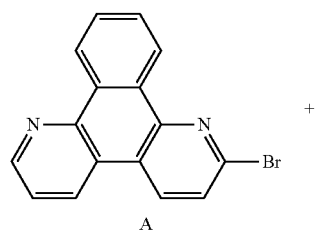

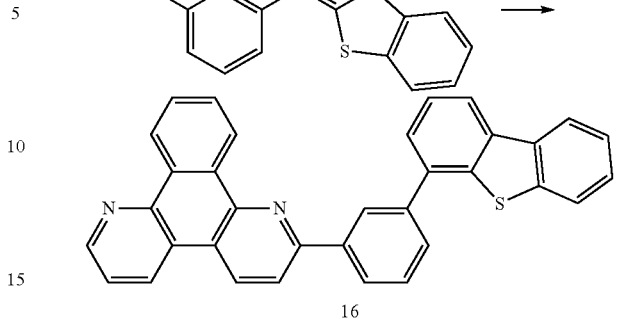

Synthesis of Compound 16

A quantity of 11.6 g of Compound 16 was synthesized with a yield of about 86.2% in the same manner as in Synthesis Example 1, except that 3-(dibenzo[b,d]thiophen-4-yl)phenylboronic acid, instead of 4-(9H-carbazol-9-yl)phenylboronic acid, was used.

Elemental Analysis for C34H20N2S: calcd C, 83.58; H, 4.13; N, 5.73; S, 6.56.

HRMS for C34H20N2S [M]+: calcd 488, found 488.

Synthesis Example 7

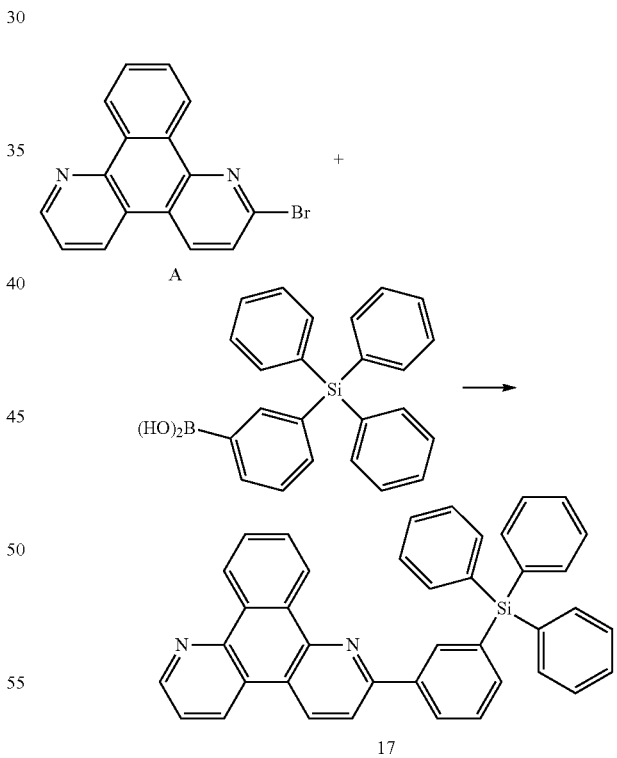

Synthesis of Compound 17

A quantity of 15.1 g of Compound 17 was synthesized with a yield of about 81.7% in the same manner as in Synthesis Example 1, except that 3-(triphenylsilyl)phenylboronic acid, instead of 4-(9H-carbazol-9-yl)phenylboronic acid, was used.

Elemental Analysis for C40H28N2Si: calcd C, 85.07; H, 5.00; N, 4.96; Si, 4.97.

HRMS for C40H28N2Si [M]+: calcd 564, found 564.

Synthesis Example 8

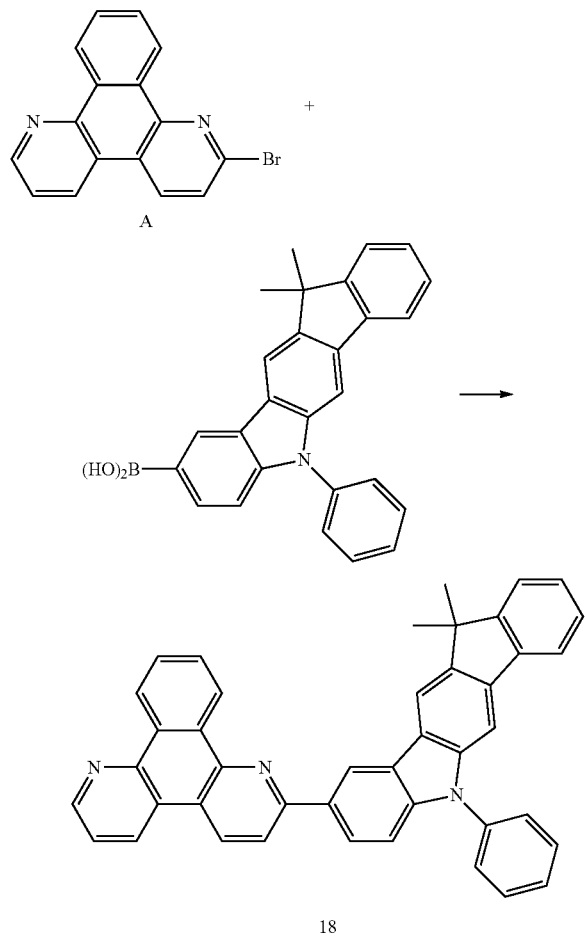

18

Synthesis of Compound 18

A quantity of 14 g of Compound 18 was synthesized with a yield of about 79.2% in the same manner as in Synthesis Example 1, except that 11,11-dimethyl-5-phenyl-5,11-dihydroindeno[1,2-b]carbazol-2-ylboronic acid, instead of 4-(9H-carbazol-9-yl)phenylboronic acid, was used.

Elemental Analysis for C43H29N3: calcd C, 87.88; H, 4.97; N, 7.15.

HRMS for C43H29N3 [M]+: calcd 587, found 587.

Synthesis Example 9

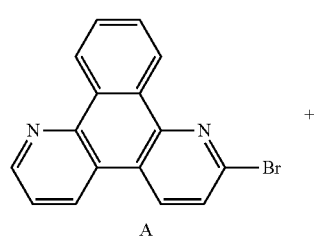

A

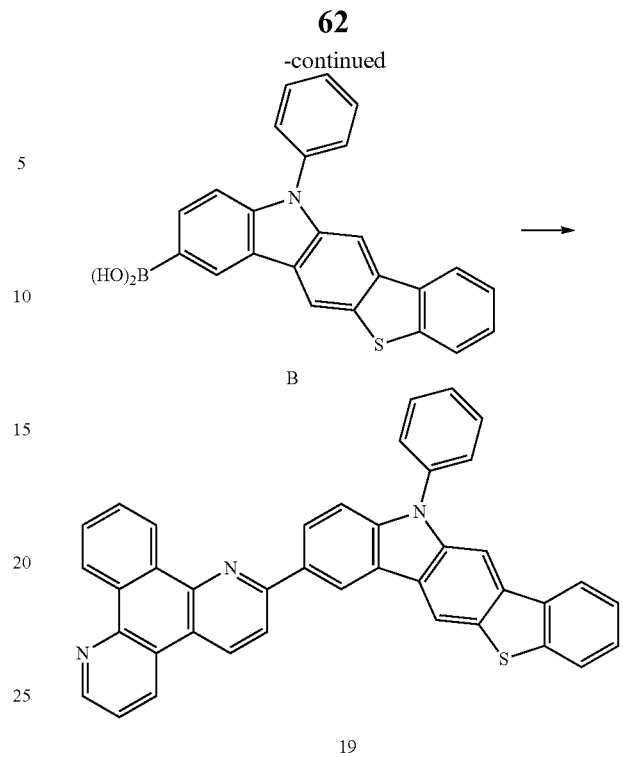

19

Synthesis of Compound 19

A quantity of 13.7 g of Compound 19 was synthesized with a yield of about 78.3% in the same manner as in Synthesis Example 1, except that Compound B, instead of 4-(9H-carbazol-9-yl)phenylboronic acid, was used.

Elemental Analysis for C40H23N3S: calcd C, 83.16; H, 4.01; N, 7.27; S, 5.55.

HRMS for C40H23N3S [M]+: calcd 577, found 577.

Synthesis Example 10

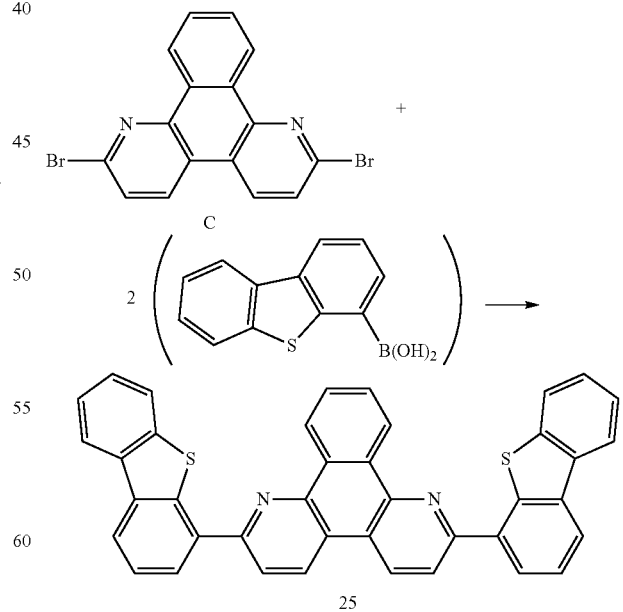

25

Synthesis of Compound 25

A quantity of 10 g (1 eq, 0.025 mol) of Intermediate C, and 12.54 g (2.1 eq, 0.055 mol) dibenzo[b,d]thiophen-4- ylboronic acid were dissolved with 500 ml of toluene in a flask. 0.57 g (0.02 eq, 0.0005 mmol) of Pd(PPh₃)₄ and 25 mL of a 2M K₂CO₃ solution were added into the solution, and then heated while stirring for about 12 hours. A reaction solution from complete reaction was filtered through Celite, and a filtered product was refined by column chromatography (MC:HEX=1:2) to obtain 10.2 g of Compound 25 with a yield of about 76.42%.

Elemental Analysis for C40H22N2S2: calcd C, 80.78; H, 3.73; N, 4.71; S, 10.78.

HRMS for C40H22N2S2 [M]+: calcd 594, found 594.

Synthesis Example 11

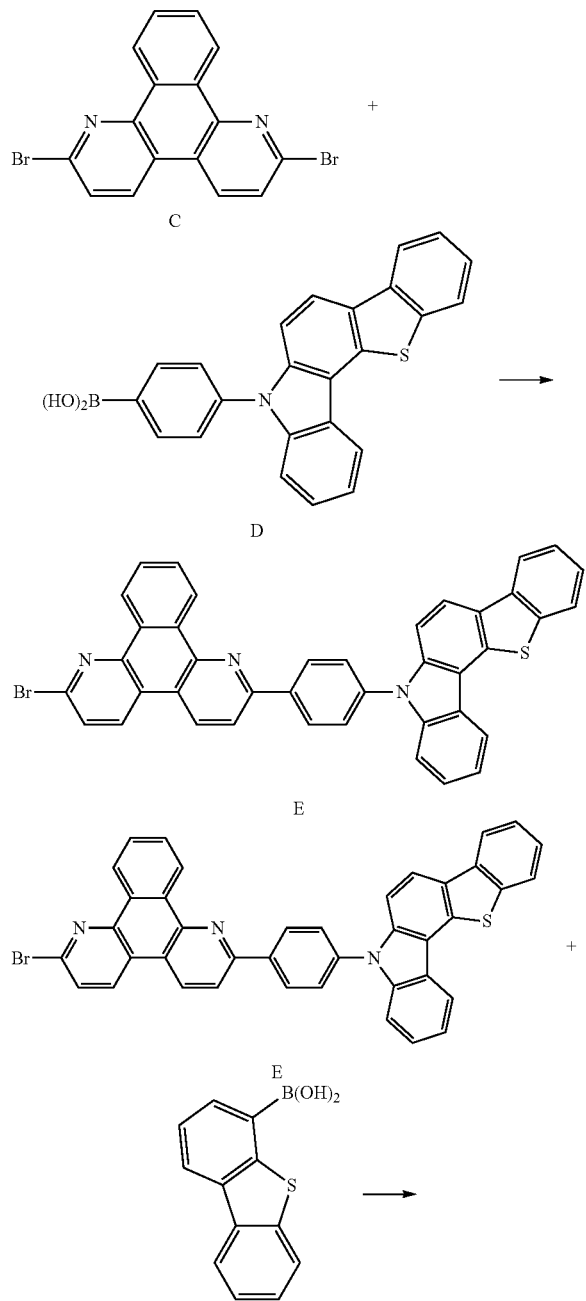

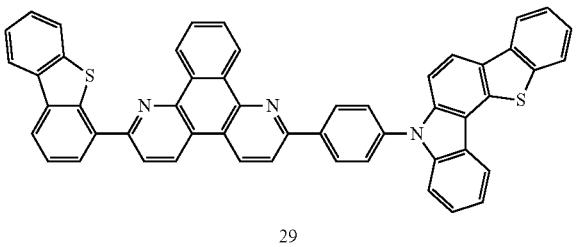

29

Synthesis of Compound E

A quantity of 10 g (1 eq, 0.025 mol) of Intermediate C, and 10.81 g (1.1 eq, 0.0275 mol) of Compound D were dissolved with 450 ml of toluene in a flask. A quantity of 0.57 g (0.02 eq, 0.0005 mmol) of Pd(PPh₃)₄ and 20 mL of a 2M K₂CO₃ solution were added into the solution, and then heated while stirring for about 12 hours. A reaction solution from complete reaction was filtered through Celite, and a filtered product was refined by column chromatography (MC:HEX=1:2) to obtain 15.1 g of Compound 25 with a yield of about 64.27%.

Elemental Analysis for C40H22BrN3S: calcd C, 73.17; H, 3.38; Br, 12.17; N, 6.40; S, 4.88.

HRMS for C40H22BrN3S [M]+: calcd 655, found 655.

Synthesis of Compound 29

A quantity of 10 g (1 eq, 0.015 mol) of Intermediate E, and 4.17 g (1.2 eq, 0.018 mol) of dibenzo[b,d]thiophen-4-ylboronic acid were dissolved with 350 ml of toluene in a flask. A quantity of 0.34 g (0.02 eq, 0.0003 mmol) of Pd(PPh₃)₄ and 17 mL of a 2M K₂CO₃ solution were added into the solution, and then heated while stirring for about 12 hours. A reaction solution from complete reaction was filtered through Celite, and a filtered product was refined by column chromatography (MC:HEX=1:2) to obtain 13.1 g of Compound 29 with a yield of about 85.29%.

Elemental Analysis for C52H29N3S2: calcd C, 82.19; H, 3.85; N, 5.53; S, 8.44.

HRMS for C52H29N3S2 [M]+: calcd 759, found 759.

Example 1

To manufacture an anode, a corning 15 Ω/cm2 (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 4,4',4"-Tris(N-(2-naphthyl)-N-phenyl-amino)-triphenylamine (2-TNATA) as a HIL material was vacuum-deposited on the glass substrate to form a HIL having a thickness of about 600 Å. Then, 4,4'-bis[N-(1-naphthyl)-N-phenylamino]biphenyl (NPB) as a hole transporting compound was vacuum-deposited on the HIL to form a HTL having a thickness of about 300 Å.

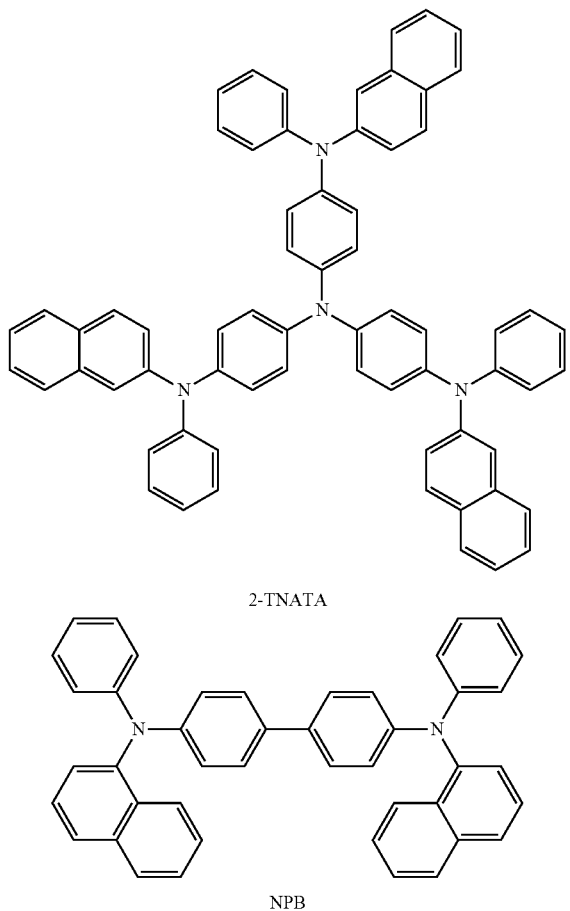

2-TNATA

NPB

Then, (piq)2Ir(acac) [bis-(1-phenylisoquinolyl)iridium (III)acetylacetonate] as a red phosphorescent dopant and Compound 1 were co-deposited in a weight ratio of 13:87 on the HTL, to form an EML with a thickness of 300 Å. Next, Alq3 was deposited on the EML to form an ETL having a thickness of about 300 Å, and Al was deposited to a thickness of 1200 Å to form an Al electrode (cathode), thereby completing the manufacture of an organic light-emitting device.

The organic light-emitting device had a driving voltage of 4.8V at a current density of 6.1 mA/cm², a luminosity of 1000 cd/m², and a luminescent efficiency of 16.5 cd/A as red emission.

Example 2

An organic light-emitting device was manufactured in the same manner as in Example 1, except that Compound 4 instead of Compound 1 was used to form the EML.

The organic light-emitting device had a driving voltage of 5.2V at a current density of 6.7 mA/cm², a luminosity of 1000 cd/m², and a luminescent efficiency of 17.4 cd/A as red emission.

Example 3

An organic light-emitting device was manufactured in the same manner as in Example 1, except that Compound 6 instead of Compound 1 was used to form the EML.

The organic light-emitting device had a driving voltage of 5.5V at a current density of 5.8 mA/cm², a luminosity of 1000 cd/m², and a luminescent efficiency of 14.7 cd/A as red emission.

Example 4

An organic light-emitting device was manufactured in the same manner as in Example 1, except that Compound 9 instead of Compound 1 was used to form the EML.

The organic light-emitting device had a driving voltage of 5.7V at a current density of 5.5 mA/cm², a luminosity of 1000 cd/m², and a luminescent efficiency of 12.5 cd/A as red emission.

Example 5

An organic light-emitting device was manufactured in the same manner as in Example 1, except that Compound 10 instead of Compound 1 was used to form the EML.

The organic light-emitting device had a driving voltage of 6.0V at a current density of 6.9 mA/cm², a luminosity of 1000 cd/m², and a luminescent efficiency of 15.9 cd/A as red emission.

Example 6

An organic light-emitting device was manufactured in the same manner as in Example 1, except that Compound 16 instead of Compound 1 was used to form the EML.

The organic light-emitting device had a driving voltage of 6.1V at a current density of 6.2 mA/cm², a luminosity of 1000 cd/m², and a luminescent efficiency of 13.9 cd/A as red emission.

Example 7

An organic light-emitting device was manufactured in the same manner as in Example 1, except that Compound 17 instead of Compound 1 was used to form the EML.

The organic light-emitting device had a driving voltage of 5.0V at a current density of 5.2 mA/cm², a luminosity of 1000 cd/m², and a luminescent efficiency of 13.1 cd/A as red emission.

Example 8

An organic light-emitting device was manufactured in the same manner as in Example 1, except that Compound 18 instead of Compound 1 was used to form the EML.

The organic light-emitting device had a driving voltage of 6.9V at a current density of 6.6 mA/cm², a luminosity of 1000 cd/m², and a luminescent efficiency of 16.4 cd/A as red emission.

Example 9

An organic light-emitting device was manufactured in the same manner as in Example 1, except that Compound 19 instead of Compound 1 was used to form the EML.

The organic light-emitting device had a driving voltage of 5.1V at a current density of 6.7 mA/cm², a luminosity of 1000 cd/m², and a luminescent efficiency of 17.0 cd/A as red emission.

Example 10

An organic light-emitting device was manufactured in the same manner as in Example 1, except that Compound 25 instead of Compound 1 was used to form the EML.

The organic light-emitting device had a driving voltage of 5.9V at a current density of 7.1 mA/cm², a luminosity of 1000 cd/m², and a luminescent efficiency of 15.1 cd/A as red emission.

Example 11

An organic light-emitting device was manufactured in the same manner as in Example 1, except that Compound 29 instead of Compound 1 was used to form the EML.

The organic light-emitting device had a driving voltage of 6.7V at a current density of 5.29 mA/cm², a luminosity of 1000 cd/m², and a luminescent efficiency of 16.3 cd/A as red emission.

Comparative Example 1

An organic light-emitting device was manufactured in the same manner as in Example 1, except that a widely known host CBP, instead of Compound 1, was used in forming the EML.

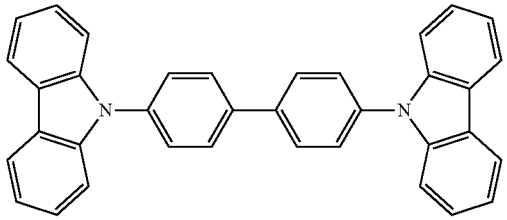

CBP

The organic light-emitting device had a driving voltage of 7.8V at a current density of 5.5 mA/cm², a luminosity of 1000 cd/m², and a luminescent efficiency of 11.2 cd/A as red emission.

The organic light-emitting devices of Examples 1 to 10, including EMLs formed using Compounds 1, 4, 6, 9, 10, 16, 17, 18, 19, 25, and 29 as a phosphorescent host, had a driving voltage lower by 20% or greater than the organic light-emitting device of Comparative Example 1 using widely known CBP, and had good I-V-L characteristics with higher efficiency. In particular, the organic light-emitting devices of Examples 1 to 10 had lifetime characteristics markedly improved by 40% or greater as compared with the organic light-emitting device of Comparative Example 1. Some of the results of the lifetime measurement using Compounds 1, 4, 6, 9, 10, 16, 17, 18, 19, 25, and 29 are shown in Table 1 below.

TABLE 1

| Example | EML material | T97 lifetime (hr @ 100 mA/cm²) |
| --- | --- | --- |
| Example 1 | Compound 1 | 970 |
| Example 2 | Compound 4 | 921 |
| Example 3 | Compound 6 | 943 |
| Example 4 | Compound 9 | 921 |
| Example 5 | Compound 10 | 991 |
| Example 6 | Compound 16 | 937 |
| Example 7 | Compound 17 | 897 |
| Example 8 | Compound 18 | 911 |
| Example 9 | Compound 19 | 956 |
| Example 10 | Compound 25 | 971 |
| Example 11 | Compound 29 | 923 |
| Comparative Example 1 | CBP | 675 |

As described above, according to the one or more embodiments of the present invention, the novel heterocyclic compound of Formula 1 above may be used as a green or red phosphorescent material with high luminescence characteristics. Therefore, organic light-emitting devices having high efficiency, low driving voltages, high luminance, and long lifetime may be manufactured using the heterocyclic compounds.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. One of Compounds 1 to 30 below:

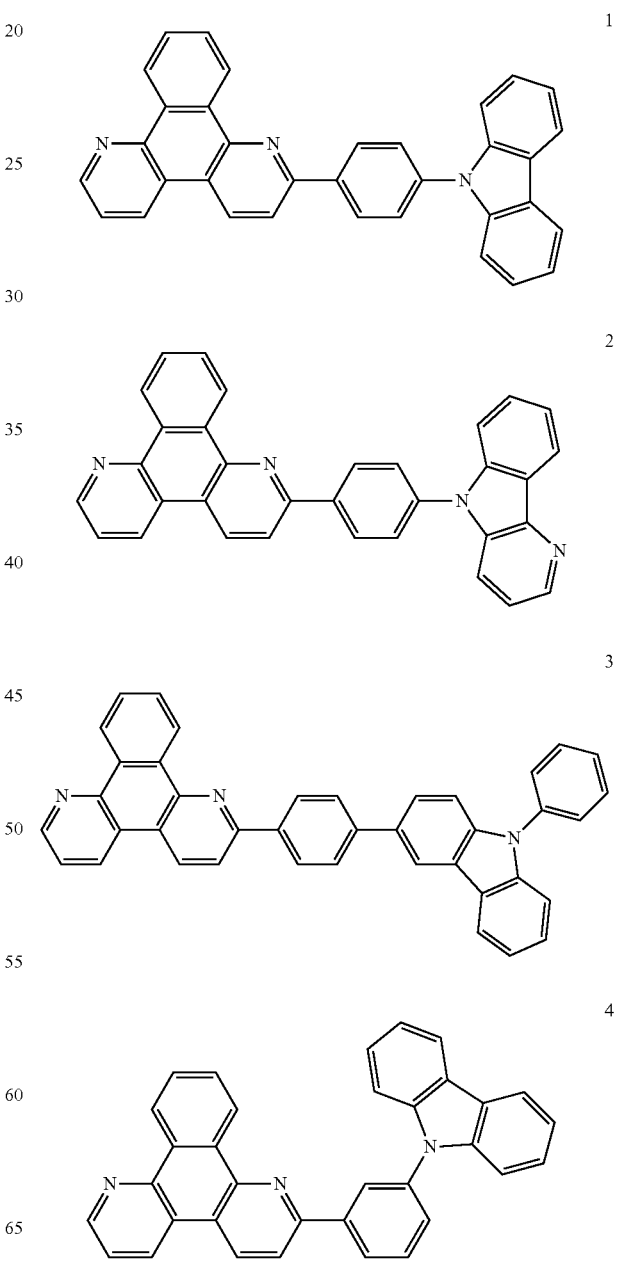

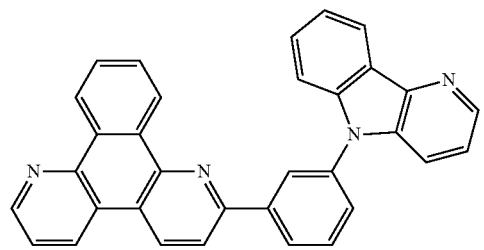
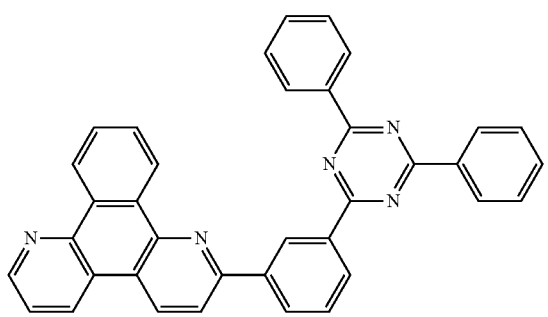
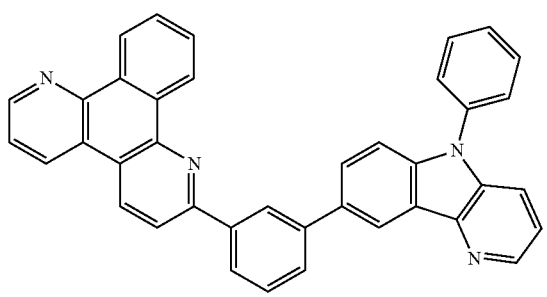
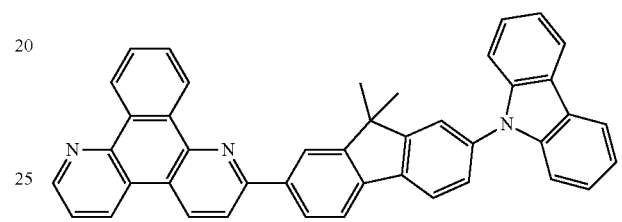
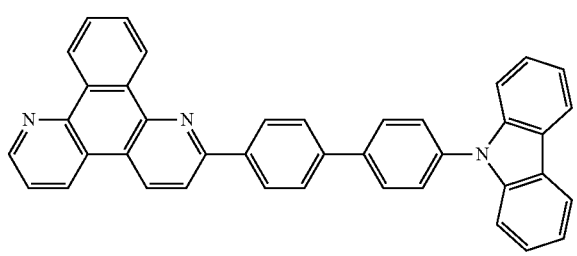
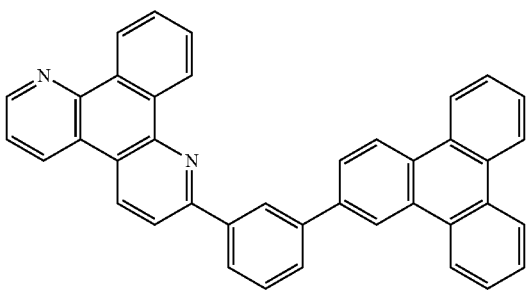
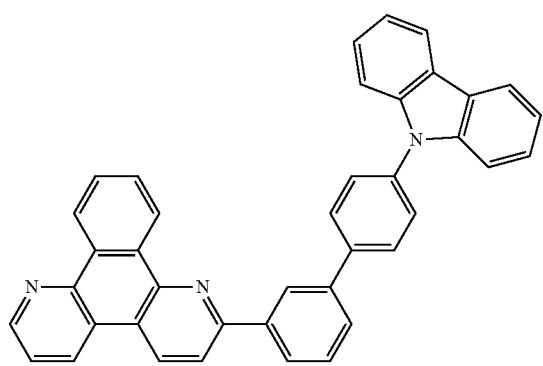
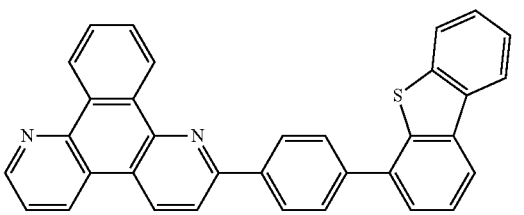
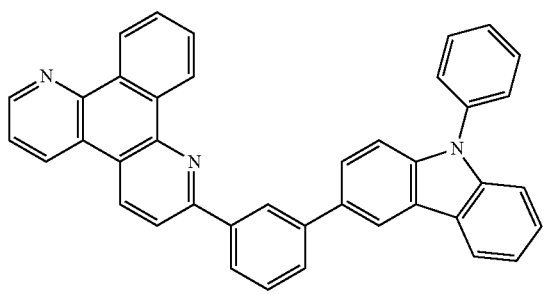
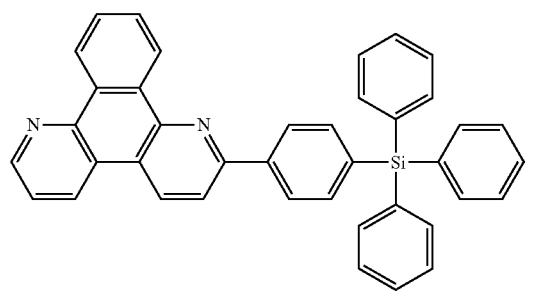

15
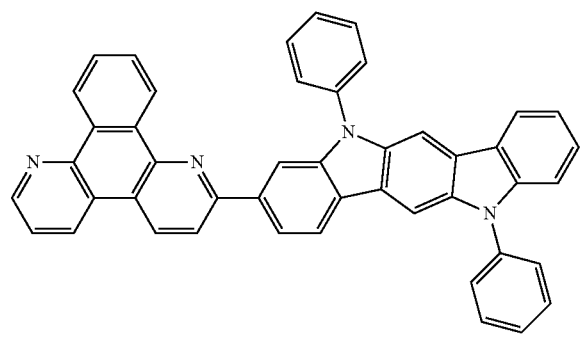
16
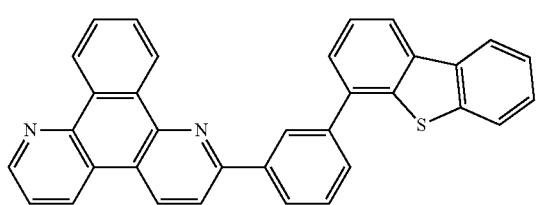
17
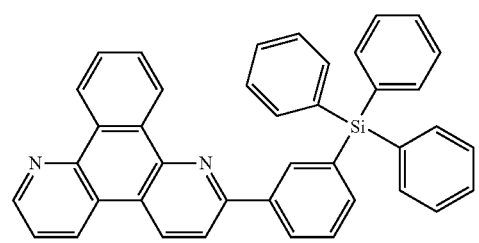
18
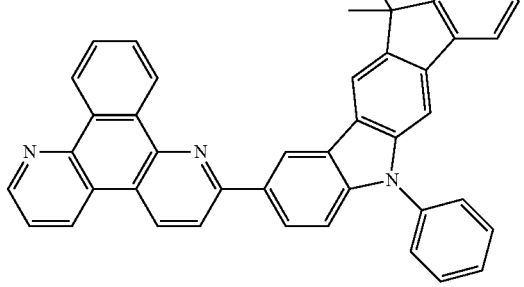
19
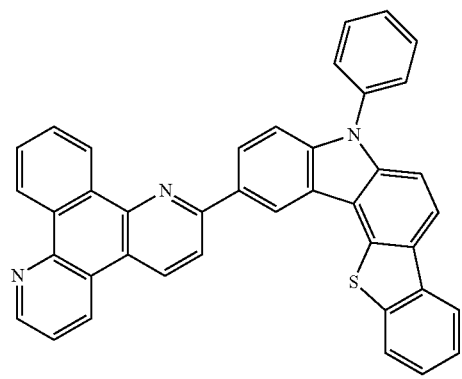
20
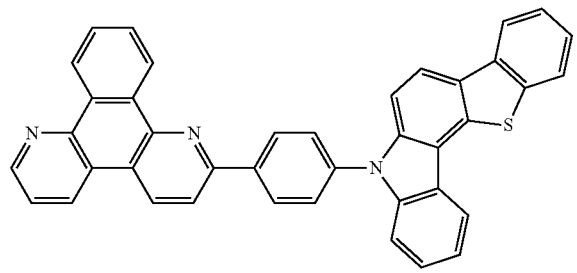
21
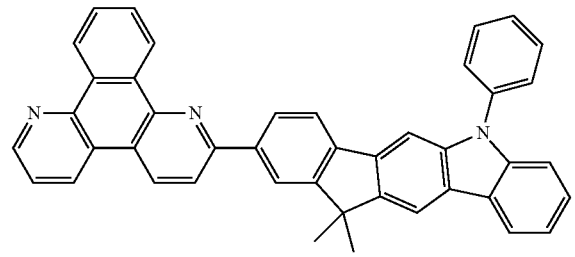
22
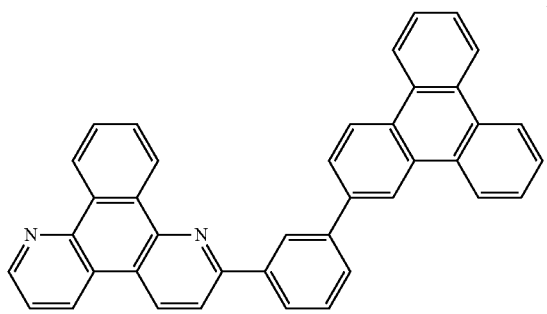
23
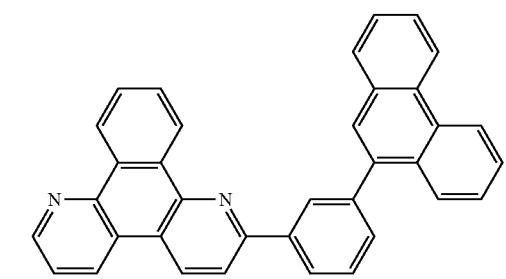
24
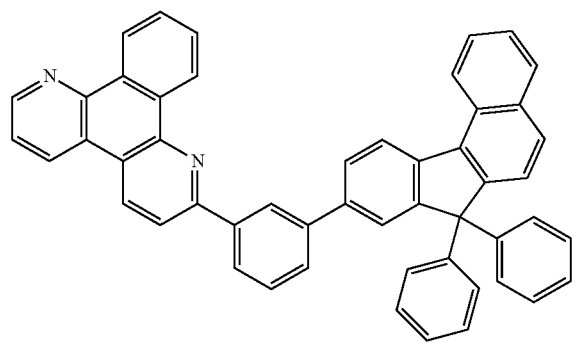

-continued

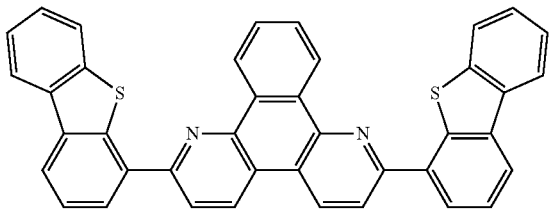
25

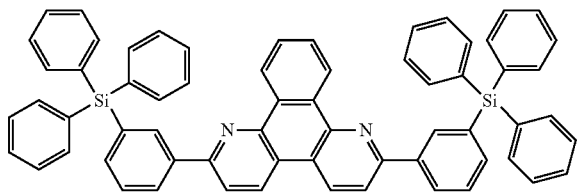
26

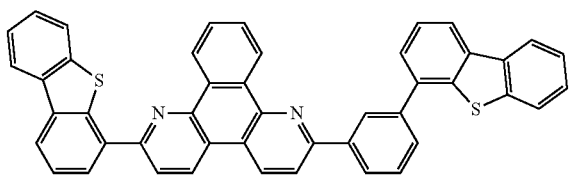
27

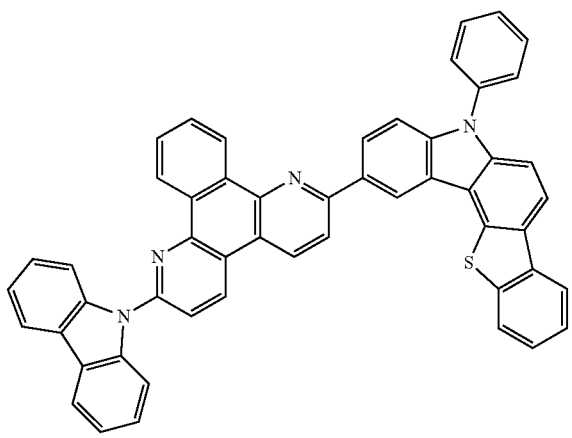
28

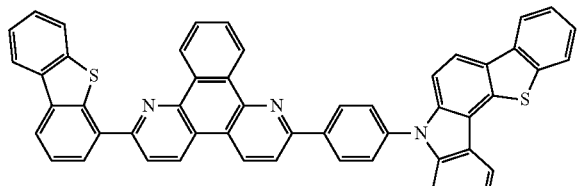
29

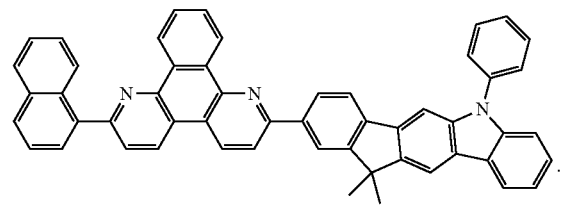
30

2. An organic light-emitting device comprising:
a first electrode;
a second electrode; and
an organic layer between the first electrode and the second electrode, the organic layer comprising a heterocyclic compound of claim 1.

3. The organic light-emitting device of claim 2, the organic layer comprising an emission layer.

4. The organic light-emitting device of claim 2, the organic light-emitting device comprising: an emission layer; at least one of an electron injection layer, an electron transport layer and a functional layer having both electron injection and transport capabilities; and at least one of a hole injection layer, a hole transport layer and a functional layer having both hole injection and transport capabilities,
the emission layer comprising the heterocyclic compound, the emission layer further comprising at least one of an anthracene-based compound, an arylamine-based compound and a styryl-based compound.

5. The organic light-emitting device of claim 2, the organic light-emitting device comprising: an emission layer; at least one of an electron injection layer, an electron transport layer and a functional layer having both electron injection and transport capabilities; and at least one of a hole injection layer, a hole transport layer and a functional layer having both hole injection and transport capabilities,
the emission layer comprising the heterocyclic compound,
the emission layer comprising red, green, blue, and white emission layers, one of which comprises a phosphorescent compound.

6. The organic light-emitting device of claim 5, at least one of the hole injection layer, the hole transport layer, and the functional layer having both hole injection and hole transport capabilities comprising a charge-generating material.

7. The organic light-emitting device of claim 6, the charge-generating material being a p-dopant.

8. The organic light-emitting device of claim 7, the p-dopant being a quinone derivative.

9. The organic light-emitting device of claim 7, the p-dopant being a metal oxide.

10. The organic light-emitting device of claim 7, the p-dopant being a cyano group-containing compound.

11. The organic light-emitting device of claim 2, the organic layer comprising an electron transport layer, the electron transport layer comprising a metal complex.

12. The organic light-emitting device of claim 11, the metal complex being a Li complex.

13. The organic light-emitting device of claim 11, the metal complex being compound 203 below:

<Compound 203>

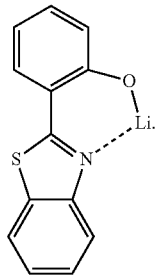

14. The organic light-emitting device of claim 2, the organic layer being formed from the heterocyclic compound using a wet process.

15. A flat panel display device comprising the organic light-emitting device of claim 2, the first electrode of the organic light-emitting device being electrically connected to one of a source electrode and a drain electrode of a thin-film transistor.

* * * * *